United States Patent
Johnson

(10) Patent No.: US 10,633,704 B2
(45) Date of Patent: Apr. 28, 2020

(54) DIAGNOSTIC AND IMMUNOTHERAPY COMPOSITIONS AND METHODS FOR DISEASE STATES MEDIATED BY INHIBITOR-RESISTANT CD8 T-CELLS

(71) Applicant: Raymond M. Johnson, Branford, CT (US)

(72) Inventor: Raymond M. Johnson, Branford, CT (US)

( * ) Notice: Subject to any disclaimer, the term of this patent is extended or adjusted under 35 U.S.C. 154(b) by 141 days.

(21) Appl. No.: 15/218,141

(22) Filed: Jul. 25, 2016

(65) Prior Publication Data

US 2017/0002419 A1  Jan. 5, 2017

Related U.S. Application Data

(63) Continuation-in-part of application No. 14/181,327, filed on Feb. 14, 2014, now abandoned, and a continuation-in-part of application No. 13/811,806, filed as application No. PCT/US2011/045212 on Jul. 25, 2011, now abandoned, said application No. 14/181,327 is a continuation-in-part of application No. 13/811,806, filed on Apr. 8, 2013, now abandoned.

(60) Provisional application No. 61/367,127, filed on Jul. 23, 2010, provisional application No. 61/764,565, filed on Feb. 14, 2013.

(51) Int. Cl.
| | | |
|---|---|---|
| C07H 21/02 | (2006.01) | |
| A61K 38/00 | (2006.01) | |
| C12Q 1/6883 | (2018.01) | |
| G01N 33/564 | (2006.01) | |
| G01N 33/577 | (2006.01) | |
| G01N 33/68 | (2006.01) | |
| G01N 33/50 | (2006.01) | |

(52) U.S. Cl.
CPC ....... *C12Q 1/6883* (2013.01); *G01N 33/5047* (2013.01); *G01N 33/564* (2013.01); *G01N 33/577* (2013.01); *G01N 33/6893* (2013.01); *C12Q 2600/106* (2013.01); *C12Q 2600/118* (2013.01); *C12Q 2600/158* (2013.01); *G01N 2333/47* (2013.01); *G01N 2800/102* (2013.01); *G01N 2800/24* (2013.01); *G01N 2800/245* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,506,126 A | 4/1996 | Seed et al. |
| 6,534,277 B1 | 3/2003 | Hancock et al. |
| 2002/0001841 A1 | 1/2002 | Kaltoft et al. |
| 2006/0159667 A1 | 7/2006 | Fowler et al. |

FOREIGN PATENT DOCUMENTS

WO   2006009114   7/2008

OTHER PUBLICATIONS

Igietseme et al., Role of T lymphocytes in the pathogenesis of Chlamydia disease. J Infect Dis 2009; 200: 926-934. USA.
Skaro et al., CD8+ cells mediate aortic allograft vasculopathy by direct killing and an interferon-gamma-dependent indirect pathway, Cardiovascular Research 2004; 65(1): 283-291 USA.
Vessie et al., Aortic allograft vasculopathy is mediated by CD8+ T cells in Cyclosporin A immunosuppressed mice, Transplant Immunology 2005; 15(1): 35-44 USA.
International Search Report related to PCT/US11/45212, published by the World Intellectual Property Organization, International Bureau dated Jan. 26, 2012 as WO2012/012797A3.
Jayarapu et al., Chlamydia-specific CD4 T cell clones control Chlamydia muridarum replication in epithelial cells by nitric oxide-dependent and -independent mechanisms, J Immunol 2010; 185(11): 6911-6920 USA.
Igietseme et al., Role of CD8+ T cells in antichlamydial immunity defined by chlamydia-specific T-lymphocyte clones, Infection & Immunity 1994; 62(11): 5195-5197 USA.
Presentation Program published by the Transplantation Society on Apr. 4, 2013, pp. 56-57 related to Poster-007 by Johnson et al. entitled "Discovery of a cyclosporine-resistant cd8 t cell receptor signaling pathway dependent on the aryl hydrocarbon receptor identifies two potential mrna biomarkers for monitoring chronic rejection", UK.

(Continued)

*Primary Examiner* — Michail A Belyavskyi
(74) *Attorney, Agent, or Firm* — Reichel Stohry Dean LLP; Natalie J. Dean

(57) ABSTRACT

A previously unknown T cell receptor (TCR) activation pathway dependent on the aryl hydrocarbon receptor conferring resistance to calcineurin inhibitors and mTOR inhibitors is disclosed, including application of this pathway to the diagnosis and treatment of certain disease states refractory to treatment with calcineurin inhibitors. This alternative TCR activation pathway uniquely exists in a subset of CD8 T cells expanded in the setting of chronic rejection or rheumatoid arthritis. Expansion of this newly discovered calcineurin and mTOR inhibitor resistant CD8 T cell subset in humans can be quantified by measuring levels of certain biomarkers in the circulating CD8 T cell pool, such as Pla2g4a, to diagnose disease states mediated thereby. Additionally, methods for diagnosing ongoing active inflammation mediated by this resistant CD8 T cell subset in either chronic rejection or rheumatoid arthritis are provided, which comprise measuring levels of the biomarker Scin in the circulating CD8 T cell pool.

9 Claims, 8 Drawing Sheets

(56) References Cited

OTHER PUBLICATIONS

Poster-007 presented by Johnson et al. on Apr. 4-6, 2013, at the 4th International Conference on Transplantomics and Biomarkers in Organ Transplantation held by the Transplantation Society, UK.

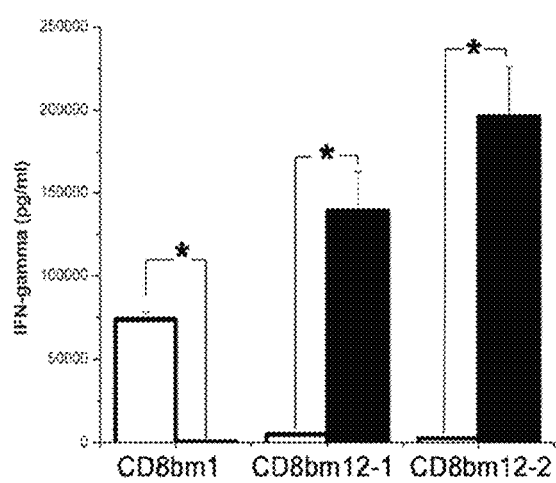 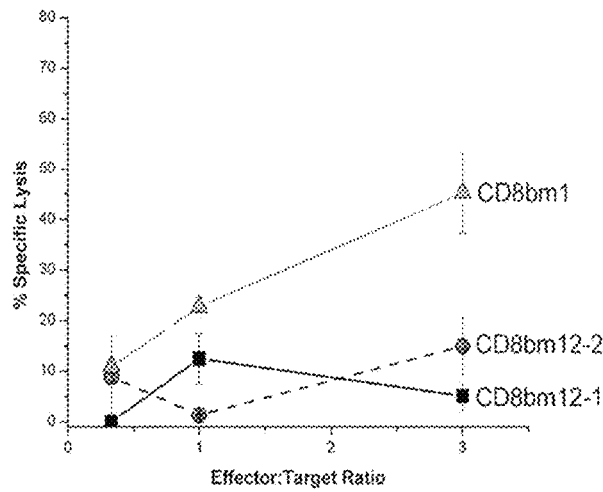
FIG. 2A  FIG. 2B
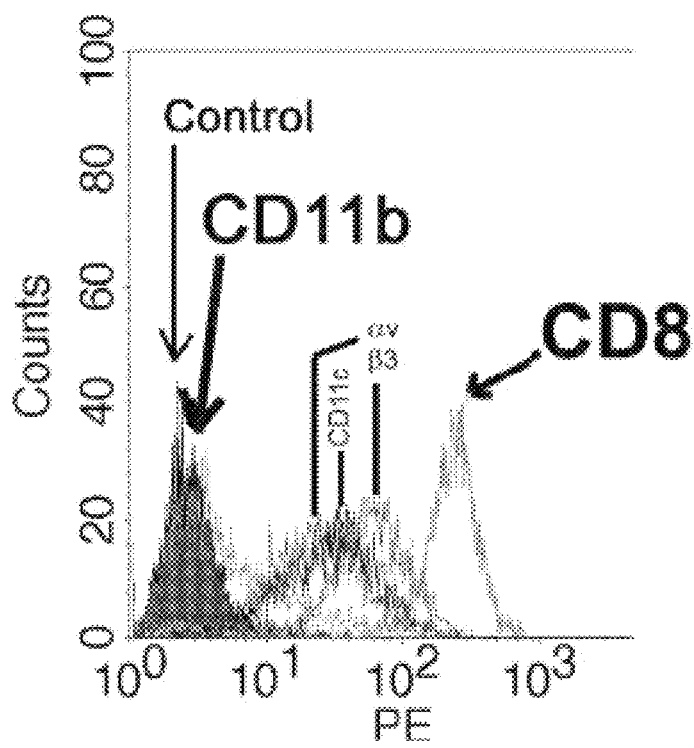
FIG. 3

DIAGNOSTIC AND IMMUNOTHERAPY COMPOSITIONS AND METHODS FOR DISEASE STATES MEDIATED BY INHIBITOR-RESISTANT CD8 T-CELLS

PRIORITY

This application (a) is related to, claims the priority benefit of, and is a U.S. continuation-in-part now-abandoned patent application of U.S. patent application Ser. No. 14/181,327 to Johnson, filed Feb. 14, 2014, which (1) is related to and claims the priority benefit of U.S. Provisional Application Ser. No. 61/764,565 to Johnson, filed Feb. 14, 2013 and (2) is related to, claims the priority benefit of, and is a U.S. continuation-in-part patent application of now-abandoned U.S. patent application Ser. No. 13/811,806 to Johnson, filed Apr. 8, 2013, which is related to, claims the priority benefit of, and is a U.S. Section 371 national stage patent application of International Application PCT/US11/45212, filed Jul. 25, 2011, which is related to and claims the priority benefit of U.S. Provisional Patent Application 61/367,127, filed Jul. 23, 2010; and (b) is related to, claims the priority benefit of, and is a U.S. continuation-in-part patent application of now-abandoned U.S. patent application Ser. No. 13/811,806 to Johnson, filed Apr. 8, 2013, which is related to, claims the priority benefit of, and is a U.S. Section 371 national stage patent application of International Application PCT/US11/45212, filed Jul. 25, 2011, which is related to and claims the priority benefit of U.S. Provisional Patent Application 61/367,127, filed Jul. 23, 2010. The contents of each of the foregoing applications are hereby incorporated in their entireties into this disclosure.

STATEMENT REGARDING FEDERALLY SPONSORED RESEARCH OR DEVELOPMENT

This invention was made with government support under NIH-K08-A1052128-01 awarded by the National Institute of Health. The United States Government has certain rights in the invention.

BACKGROUND

Modern immunosuppressive regimens based on immunosuppressive modalities such as calcineurin and mTOR inhibitors have improved survival and reduced morbidity in solid organ and bone marrow transplant patients. Current one-year solid organ graft survival rates are ~90%. Acute rejection is no longer a major cause of organ failure and death; instead late organ failure due to chronic rejection has become the major hurdle impeding long-term graft survival.

Chronic allograft rejection, which manifests as progressive and irreversible damage to the graft from attack due to host immune responses, is the leading cause of graft failure after the first postoperative year. For example, 50% of lung and heart transplant patients have graft attrition at 5 and 10 years post-transplant, respectively, with roughly 50% of lung transplant patients having bronchiolitis obliterans syndrome (BOS) by year 5, and 50% of surviving cardiac transplant patients having chronic allograft vasculopathy (CAV) by year 8. Additionally, the frequency of chronic graft versus host disease (GVHD) in allogeneic bone marrow transplantation is roughly 50% by year 2. The duration of graft survival has remained essentially unchanged since cyclosporine was approved for use by the U.S. Food and Drug Administration in 1983, vividly demonstrating that chronic rejection continues unabated during treatment with available immunosuppressive inhibitors of calcineurin and mTOR.

Unlike acute rejection, chronic rejection is a gradual process of deterioration and failure that occurs later in the life of the transplant. The dramatic progression of cellular infiltration and allograft destruction seen with acute rejection is less pronounced in chronically rejected grafts. However, in contrast to treatable acute rejection, chronic rejection is conventionally irreversible when histologically detected, not preventable by any immunosuppressive regimen, and its pathogenesis is not conventionally understood. In solid organ transplants, chronic allograft rejection is characterized by progressive fibrosis and intimal proliferation rather than the acute inflammation and necrosis seen in acute rejection.

The immunopathology underlying chronic rejection has been investigated using small animal models. For example, there are mouse models for BOS based on heterotopic tracheal transplantation and bone marrow transplantation. An orthotopic/heterotopic trachea transplant model has elegantly shown that allogeneic airway epithelial cells are the primary target of the T cell response and, absent immunosuppression, both CD4 and CD8 T cells mediate rejection. A rat orthotopic lung allo-transplant model incorporating cyclosporine A (CsA) and rapamycin treatment reproduced the histopathology of BOS; similarly, rapamycin was ineffective in preventing CAV in a rat cardiac transplant model. The rodent model data are consistent with the clinical experience that current immunosuppressive drugs, including mTOR inhibitors that block IL-2 receptor signaling, do not effectively inhibit all of the T cell subset(s) mediating chronic rejection.

As previously noted, to date, the mechanism underlying chronic rejection has been poorly understood. To better understand why conventional immunosuppressive therapies that are so effective against acute rejection, but remain ineffective in preventing and/or treating chronic rejection, studies have focused on host immune response evoked by allograft transplants. In particular, intensive investigations in murine CAV models have provided some insight into an effector T cell subset mediating chronic allograft rejection. Primed CD8 T cells were sufficient to cause vasculopathy in completely MHC-mismatched aortic grafts in mice treated with cyclosporine. Intimal proliferation was independent of allo-MHC class I on the aortic graft, implying CD8 recognition of allo-MHC class II molecules. Similarly, in a nude mouse model, adoptive transfer of naïve CD8 T cells was sufficient to cause CAV in MHC class II-mismatched bm12 cardiac allografts; again implying CD8 recognition of allo-MHC class II molecules. In the latter study, CAV was dependent on IFN-γ, but not perforin or Fas ligand. An important study showed that CsA prevented vasculopathy caused by CD4 T cells, but was ineffective in preventing vasculopathy caused by CD8 T cells. Accordingly, at least in mice, CD8 T cells rather than CD4 T cells appear to have a calcineurin-independent pathway for T cell activation during chronic allograft rejection. Furthermore, conventional literature supports a central role for allogeneic epithelial cells as targets for chronic allograft rejection, and CD8 T cells making IFN-γ as effectors of chronic allograft rejection in the presence of calcineurin inhibitors.

Currently, chronic rejection is diagnosed by histopathological analysis, which typically requires an invasive biopsy of the allograft. These procedures are complex and often carry risks of bleeding, infection, or tissue perforation. Biopsy results may also be subject to interpretation and reproducibility issues due to sampling errors and inter-observer variabilities as the pathological criteria used to establish the diagnosis of chronic rejection (including the thickening of an intimal layer with luminal narrowing and fibrosis). Although less invasive imaging techniques have been developed for monitoring some forms of allograft rejection, these alternatives are also susceptible to limitations similar to those associated with biopsies.

Accordingly, a need exists for an accurate and easy-to-use tool for early prognosis and follow-up of chronic rejection, particularly for early prognosis of chronic rejection before any overt clinical or histological manifestation.

BRIEF SUMMARY

The present disclosure provides methods for the diagnosis and treatment of certain disease states mediated by a subset of CD8 T cells with a Ahr-dependent TCR activation pathway in the presence of calcineurin and/or mTOR inhibitors, which may include (without limitation) inflammatory disease states such as chronic allograft rejection and rheumatoid arthritis. In at least one exemplary embodiment, a method of diagnosing a condition in a subject comprises the steps of purifying a population of CD8 T cells collected from peripheral blood of a subject; isolating RNA from the purified CD8 T cells; and quantifying a level of expression of a Scin biomarker in the isolated RNA. In such embodiments, any expression of the Scin biomarker is indicative of the subject experiencing an active condition mediated by a subset of CD8 T cells that are resistant to calcineurin and mTOR inhibitors. Furthermore, in at least one embodiment, the step of purifying a population of CD8 T cells may be performed using magnetic bead purification and/or the step of quantifying a level of expression of a Scin biomarker may further comprise performing reverse transcription polymerase chain reaction on the isolated RNA and producing a semi-quantitative visualization of the level of expression of the Scin biomarker on ethidium bromide-containing agarose gels. In certain embodiments, the quantified level of expression of the Scin biomarker is indicative of the subset of CD8 T cells proliferating through an Ahr-dependent T-cell receptor signaling pathway.

The population of CD8 T cells may comprise a circulating CD8 T cell population from a mononuclear cell fraction taken from the peripheral blood of the subject. Additionally or alternatively, the subject may be a human and the Scin biomarker may be a human biomarker. As previously noted, in at least one embodiment, the active condition is an active inflammatory disease state comprising active chronic allograft rejection or rheumatoid arthritis.

Still further, in certain embodiments of the methods disclosed herein, the step of purifying a population of CD8 T cells is performed using a cell sorting technique and/or the step of quantifying a level of expression of a Scin biomarker further comprises quantifying the level of expression of the Scin biomarker at a mRNA level using real-time RT-PCR or at a protein level using enzyme-linked immunosorbent assay. Alternatively, the step of quantifying a level of expression of a Scin biomarker may further comprise utilizing flow cytometry gated on CD8 T cells to measure intracellular frequency and/or levels of the Scin biomarker.

Additional methods for diagnosing a condition in a subject using additional biomarkers are also provided. In at least one exemplary embodiment, such methods comprise the steps of: quantifying a level of expression of at least one biomarker in a CD8 T cell population of the subject, the CD8 T cell population collected from peripheral blood of the subject; and, if the level of expression of the biomarker indicates expression of the biomarker, comparing the quantified level of expression with a baseline level of expression established for such biomarker. There, an elevated level of expression as compared to the baseline is indicative of expansion of a subset of activated CD8 T cells refractory to calcineurin and mTOR therapy within the CD8 T cell population and the subject experiencing a disease state mediated by such subset of activated CD8 T cells. In such embodiments, one or more of the at least one biomarkers comprises Scin, Rasgrp3, Pla2g4a, Padi2, Mest, Klh16, Sgk3 and/or Prkcz. In at least one embodiment, the subject comprises a human and the at least one biomarker comprises a human biomarker.

Furthermore, in certain exemplary embodiments, the subject comprises a human and one of the biomarkers comprises the Pla2g4a biomarker. There, the disease state may comprise an inflammatory disease state selected from the group consisting of chronic allograft rejection and rheumatoid arthritis. Additionally or alternatively, the level of expression of the Pla2g4a biomarker may be correlative to a degree of expansion of the subset of CD8 T cells within the CD8 T cell population refractory to calcineurin and mTOR therapy, and thereby the subject's risk for developing CsA/rapamycin refractory illness. In at least one exemplary embodiment, the inflammatory disease state comprises burned-out chronic allograft rejection with future risk of accelerated chronic rejection in the setting of re-transplantation.

In some embodiments of the method disclosed herein, the step of quantifying a level of expression of at least one biomarker may further comprise the steps of purifying the population of CD8 T cells and isolating RNA from the purified population of CD8 T cells. Additionally, in such embodiments, the step of quantifying a level of expression of at least one biomarker may also comprise quantifying a level of expression of one or more of the at least one biomarkers at a mRNA level using real-time RT-PCR or at a protein level using enzyme-linked immunosorbent assay.

Still further, in at least one exemplary embodiment of the method, the at least one biomarker may comprise both a Scin biomarker and the Pla2g4a biomarker. There, any quantified expression of the Scin biomarker will be indicative of activation of the subset of CD8 T cells refractory to calcineurin and mTOR therapy within the CD8 T cell population, thereby identifying the disease state being active and requiring an adjustment in immunosuppressive therapy.

As detection of elevated levels of expression of the biomarkers described herein are indicative of a subset of activated CD8 T cells refractory to calcineurin and mTOR therapy within the CD8 T cell population proliferating through the newly discovered Ahr-dependent TCR activation pathway described herein, such concepts may additionally be used to predict a subject's responsiveness to different types of immunotherapy. For example, if such Ahr-dependent TCR activation pathway is utilized in the presence of calcineurin and/or mTOR inhibitors, treatment of the subject with conventional immunosuppression therapies alone will not be effective to treat and/or prevent the underlying condition or disease state (e.g., chronic allograft rejection and/or rheumatoid arthritis). Indeed, the Ahr-dependent TCR activation pathway must also be blocked by an antagonist of Ahr, for example.

Accordingly, the present disclosure also provides methods for predicting responsiveness of a subject to immunotherapy comprising the steps of: quantifying a level of expression of at least one biomarker in a CD8 T cell population of the subject, the CD8 T cell population collected from peripheral blood of the subject; comparing the level of expression of the at least one biomarker with a baseline level of expression established for such biomarker; and identifying if the subject is likely to be a responder or non-responder to solely a calcineurin and/or mTOR therapy based on the comparison with the baseline level. In at least one exemplary embodiment, one or more of the at least one biomarker comprises Scin, Rasgrp3, Pla2g4a, Padi2, Mest, Klh16, Sgk3 and/or Prkcz. There, if an elevated level of expression of the biomarker as compared to its respective baseline, it is indicative that a subset of activated CD8 T cells refractory to calcineurin and mTOR therapy within the CD8 T cell population is proliferating through an Ahr-dependent T-cell receptor signaling pathway and the subject is experiencing a disease state mediated by such subset of activated CD8 T cells. As such, if elevated expression of such biomarkers is detected, a diagnosis can be made that the subject is experiencing such a disease state. In at least one exemplary embodiment of the method of predicting responsiveness described herein, the subject is a human and the at least one biomarker is a human biomarker.

BRIEF DESCRIPTION OF THE FIGURES

The disclosed embodiments and other features, advantages, and aspects contained herein, and the manner of attaining them, will become apparent in light of the following detailed description of various exemplary embodiments of the present disclosure. Such detailed description will be better understood when taken in conjunction with the accompanying drawings, wherein:

FIG. 2A shows bar graphs of pg ml$^{-1}$ of IFN-gamma produced by CD8 alloreactive T-cell clones recognizing either Bm1.11 (white bars) or Bm12.4 (black bars), demonstrating the specificity of the T cell clones. Bm1.1 is an epithelial cell line derived from a bm1 mouse; Bm12.4 is an epithelial cell line derived from a bm12 mouse; both cell lines are novel reagents derived by the inventor. CD8bm1 is a conventional CsA-sensitive CD8 T cell clone specific for the allo-MHC class I molecule H-2 K$^{bm1}$. CD8Bm12-1 is the cyclosporine/rapamycin (CsA/RAPA) resistant CD8 T cell clone specific for allo-MHC class II molecule I-A$^{bm12}$ central to this disclosure. CD8bm12-2 was a second bm12-specific CD8 T cell not further studied because of poor growth characteristics in culture. *=p value<0.001.

FIG. 2B shows a cytolysis assay demonstrating that CD8bm12-1 and CD8bm12-2 are non-cytolytic as compared to conventional CD8bm1 against their respective allo-epithelial targets.

FIG. 3 shows flow cytometry data measuring cell surface phenotypes of the T-cell clone CD8bm12-1 and evidencing that CD8bm12-1 is a CD8 T cell clone.

FIG. 6B=the results of experiment 2. Proliferation of conventional CD8 T cell clone CD8bm1 is completely inhibited by CsA concentrations between 0.03 and 0.1 ug/ml. CD8bm12-1 retrains 69-75% of its proliferation at CsA concentrations up to 1 ug/ml.

FIG. 11b demonstrates that costimulation with CD28 does not overcome inhibition of CD8bm12-1 proliferation by combined inhibition of calcineurin (CsA) and AHR (CH-223191).

Figure 1:
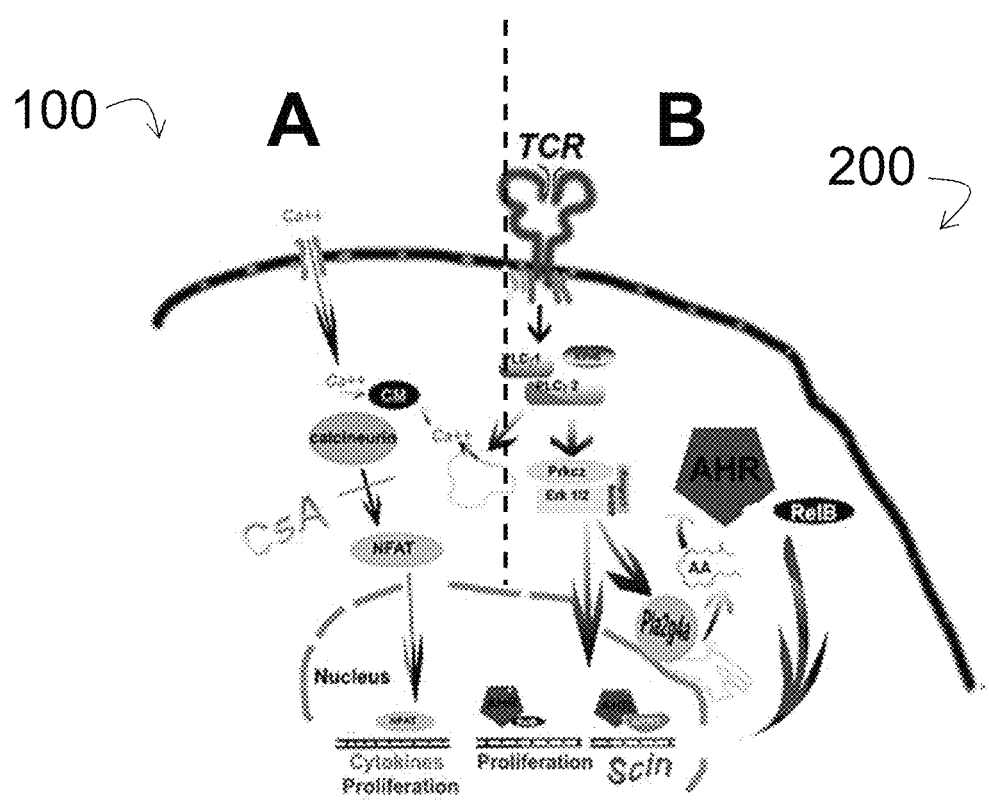
FIG. 1 illustrates a pictorial representation of the components of the conventionally known TCR signaling pathway (subpart A) and the components of the novel, Ahr-dependent, CsA/RAPA-resistant TCR signaling pathway of the present disclosure (subpart B).

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, many modifications and other embodiments of the technology described herein will come to mind to one of skill in the art to which the present disclosure pertains having the benefit of the teachings presented in the present descriptions and associated figures. Therefore, it is understood that this disclosure covers any such alternatives, modifications, and equivalents as may be included within the spirit and scope of this application as defined by the specification and appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

As used herein, the term "allograft" refers to a graft (organ or tissue) transplanted from two genetically different subjects of the same species. The subject receiving the allograft is the "recipient," while the subject providing the allograft is the "donor." A tissue or organ allograft may alternatively be referred to as a "transplant," a "graft," a "donor tissue" or a "donor organ," or using similar terms.

As used herein, "acute transplant rejection" means the rejection by the immune system of a tissue transplant recipient when the transplanted organ or tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as cyclosporine A, rapamycin, and the like.

As used herein, "chronic rejection" or "chronic allograft rejection" refers to allograft rejection, which generally within several months to years after engraftment, even in the presence of successful immunosuppression of acute rejection. Fibrosis is a common factor in chronic rejection of all types of organ and tissue transplants. Chronic rejection can typically be described by a range of specific disorders that are characteristic of the particular organ, including, for example and without limitation, BOS in lung transplants (fibroproliferative destruction of the airway) and CAV in heart transplants or transplants of cardiac tissue.

"Transplant rejection" as used herein encompasses both acute and chronic transplant rejection.

The term "therapeutically effective dose" according to the present disclosure (and unless specifically stated otherwise) means a quantity of a compound which, when administered either one time or over the course of a treatment cycle affects the health, wellbeing or mortality of a subject (e.g., and without limitation, delays the onset of and/or reduces the severity of one or more of the symptoms associated with chronic allograft rejection). The amount of the disclosed compound to be administered to a transplant recipient will depend on the type of transplant, the characteristics of the patient or subject (such as general health, age, sex, body weight, and tolerance to drugs).

A "subject" or "patient," as used herein, is a mammal, preferably a human, but can also be an animal who has received a tissue transplant and is in need of treatment to inhibit transplant rejection and preferably chronic transplant rejection.

A "marker" or "biomarker" as the terms are used herein may be described as being differentially expressed when the level of expression in a subject who is rejecting an allograft is significantly different from that of a subject or sample taken from a non-rejecting subject. A differentially expressed marker may be overexpressed or underexpressed as compared to the expression level of a normal or control sample or subjects' baseline. The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index (e.g., a non-rejection cutoff index). Alternatively, the relative abundance of the marker or markers may be determined relative to a control, which may be a clinically normal subject (e.g., one who has not received an allograft) or may be an allograft recipient that has not previously demonstrated active rejection.

A "profile" or "assay" is a set of one or more markers and their presence, absence, and/or relative level or abundance (relative to one or more controls). For example, a cytokine profile is a dataset of the presence, absence, relative level or abundance of cytokines present within a sample. A genomic or nucleic acid profile is a dataset of the presence, absence, relative level or abundance of expressed nucleic acids (e.g., transcripts, mRNA, or the like). A profile may alternatively be referred to as an expression profile.

"Down-regulation" or "down-regulated" may be used interchangeably and refer to a decrease in the level of a marker, such as a gene, nucleic acid, metabolite, transcript, protein, or polypeptide. "Up-regulation" or "up-regulated" may also be used interchangeably and refer to an increase in the level of a marker, such as a gene, nucleic acid, metabolite, transcript, protein, or polypeptide. Also, a pathway, such as a signal transduction or metabolic pathway may be up- or down-regulated.

Of significance of the present disclosure, at least in part, is not the particular methods used to detect the marker or set of markers, but what the markers are used to detect. As previously noted, there are many methods that may be used to detect the expression, quantification, or profile of one or more biomarkers. Once the marker or set of markers to be detected or quantified is identified, any of several techniques (that are now known or hereinafter developed) may be used, with the provision of appropriate reagents. One of skill in the art, when provided with the one or more biomarkers to be identified, will be capable of selecting the appropriate assay (e.g., a PCR-based or a microassay-based assay for nucleic acid markers, an ELISA, protein or antibody microarray or similar immunologic assay, etc.) for performing the methods disclosed herein.

Methods of producing antibodies for use in protein or antibody arrays, or other immunology based assays are known in the art. Once the marker or markers are identified, one of skill in the art will be able to use such information to prepare one or more appropriate antibodies and perform the selected assay. For preparation of monoclonal antibodies directed towards a biomarker, any technique that provides for the production of antibody molecules by continuous cell lines in culture may be used. For example, but without limitation, human antibodies may be used and can be obtained by transforming human B cells with EBV virus in vitro, using a hybridoma technique, or as is otherwise known in the art. Likewise, polyclonal antibodies (or a fragment thereof) can be raised according to known methods by administering the appropriate antigen or epitope to a host animal (e.g., a pig, cow, horse, rabbit, goat, sheep, mice, etc.). Antibodies useful in practicing the present disclosure may be polyclonal or monoclonal antibodies unless specifically described as one or the other herein.

The term "collect" used in reference to certain cell types includes cell populations that have been enriched in a particular type of cells. Enriched cell populations may include more cells of a particular type of cell in the population than are found in healthy physiological sources.

The use of the disclosed compounds and methods to inhibit, diagnose, and/or treat transplant rejection, e.g., chronic transplant rejection, is not limited to any particular organ or tissue type. The disclosed compounds and methods are effective, but not limited to, inhibiting rejection of transplanted heart, lung, kidney, liver, skin, trachea, bone, bone marrow, bladder or parts thereof.

As used herein, "immunosuppressant drugs" means and incudes any drugs now known or hereinafter developed that are used for the treatment of allograft rejection. These include, for example and without limitation, calcineurin inhibitors such as cyclosporine (CsA) and tacrolimus (FK-506), mTOR inhibitors such as rapamycin (RAPA), and others such as azathioprine, methylprednisolone, deoxypergualin, and mycophenylate, with conventional techniques employing CsA or tacrolimus as the basis of most immunosuppressive protocols. Furthermore, while particular compounds are used herein to describe the methods and inventive concepts of the present disclosure, it will be appreciated that the present disclosure is not limited to those particular compounds and is inclusive of all effectively similar substitutes. For example, and without limitation, certain embodiments hereof utilize the CH-223191 Ahr antagonist; however, it will be appreciated that any other ligand-selective antagonist of Ahr may be employed.

The compounds described herein, and the pharmaceutically acceptable salts thereof, can be used in pharmaceutical preparations in combination with a pharmaceutically acceptable carrier or diluent. For example, cyclosporine may also include salts of compounds having the formula (E)-14,17,26,32-tetrabutyl-5-ethyl-S-(1-hydroxy-2-methylhex-4-enyl)-1,3,9,12,15,1S,20,23,27-nonamethyl-11,29-dipropyl-1,3,6,9,12,15,1S,21,24,27,30-undecaazacyclodotriacontan-2,4,7,10,13,16,19,22,25,2S,31-undecaone, although other related molecules may also be used to practice some aspects of the invention. The terms, 'Cyclosporin' and 'Cyclosporine' may both used as neither appears to be the preferred term of art in the literature. Likewise, rapamycin may also include salts of compounds having the formula (3 S,6R,7E,9R,10R,12R,14S,15E,17E, 19E,21S,23 S,26R, 27R,34aS)-9,10,12,13,14,21,22,23,24,25,26,27,32,33,34, 34a-hexadecahydro-9,27-dihydroxy-3-[(1R)-2-[(1S,3R, 4R)-4-hydroxy-3-methoxycyclohexyl]-1-methylethyl]-10, 21-dimethoxy-6,S,12,14,20,26-hexamethyl-23,27-epoxy-3H-pyrido[2,1-c][1,4]oxaazacyclohentriacontine-1,5,11,2S, 29(4H,6H,31H) pentone. Suitable pharmaceutically acceptable carriers include inert solid fillers or diluents and sterile aqueous or organic solutions. The compounds will be present in such pharmaceutical compositions in amounts sufficient to provide the desired dosage amount in the ranges described herein. For oral administration, the disclosed compounds or salts thereof can be combined with a suitable solid or liquid carrier or diluent to form capsules, tablets, pills, powders, syrups, solutions, suspensions and the like. Tablets, pills, capsules, and the like contain from about 1 to about 99 weight percent of the active ingredient and a binder, excipients, a disintegrating agent, a lubricant, and/or a sweetening agent (as are known in the art).

The term "lymphocyte" means a nucleated or "white" blood cell (leukocyte). Lymphocytes include T-cells, B-cells, and the like, and other immune regulatory cells.

A "T-cell" or "T cell" is a class of lymphocyte responsible for cell-mediated immunity and for stimulating B-cells. A stimulated B-cell produces antibodies for specific antigens. Both T-cells and B-cells function to recognize non-self antigens in a subject. Non-self-antigens include those of viruses, bacteria, and other infectious agents, as well as allografts. T-cell based immune response can occur either directly, by cross reaction with allogeneic major histocompatibility complex (MHC) molecules, or indirectly (by reaction with allogeneic peptide fragments bound to host MHC molecules on antigen-presenting cells or allogeneic target cells). T-cells not only initiate the immune response, but also mediate antigen-specific effector responses. In addition, T-cells secret soluble factors to regulate the activity of other leukocytes. For example, activated T-helper cells produce interleukins, gamma interferon, and leukotrienes. This cascade of immunoregulators acts to stimulate the attack of cytotoxic T-lymphocytes on the allograft (or other target).

A "T cell antigen receptor" or a "TCR" complex comprises a ligand-binding subunit that participates in T-cell activation upon the presentation of an antigen peptide bound to the MHC (class I or class II) residing on antigen-presenting cells (APCs). Co-stimulatory receptors, for example and without limitation CD28, CD4, and CD8, contribute to signal transduction by modulating the response threshold. All of the aforementioned components (along with any accessory proteins essential for MHC) are a part of the immunological synapse that initiates T-cell activation.

"TCR activation" means the signaling cascade that results from the activation of a T cell that may result in cytolysis, cytokine production, T cell proliferation, and/or T cell differentiation.

Embodiments of the present disclosure provide various methods and techniques relating to the detection and treatment of several disease states (including, without limitation, chronic allograft rejection and rheumatoid arthritis) based on a newly identified CsA/RAPA-resistant, IL-2-independent proliferation pathway underlying calcineurin-inhibitor refractory disease states. Accordingly, at least in part, the present disclosure details the application of this novel pathway to the detection and treatment of chronic allograft rejection and rheumatoid arthritis. Perhaps more specifically, certain embodiments of the methods provided herein facilitate the treatment of chronic allograft rejection by identifying a novel cyclosporine- and/or rapamycin-resistant TCR signaling pathway dependent on the aryl hydrocarbon receptor (Ahr) and, specifically, by using one or more human biomarkers to identify elevated levels of a cyclosporine- and rapamycin-resistant CD8 T cell subset. Furthermore, various methods are disclosed for diagnosing, treating, and monitoring disease activity in humans, including rheumatoid arthritis and chronic allograft rejection.

In brief, this novel signaling pathway was identified in light of the importance in chronic rejection animal models of: a) epithelial cells; b) bm12-mismatched transplantation, and c) CD8 T-cells. A novel T cell culture system was developed based on allogeneic bm12 skin transplantation that incorporated in vitro T-cell expansion on bm12-origin epithelial cells (i.e. a novel reagent developed by the inventor hereof and more specifically described in Jayarapu K, Kerr M, Ofner S. Johnson R M. *Chlamydia-specific CD4 T cell clones control Chlamydia muridarum replication in epithelial cells by nitric oxide-dependent and independent mechanisms*, J Immunol 2010; 185(11): 6911-20 (the "Jayarapu Publication"), which is hereby incorporated by reference in its entirety). This novel experimental system allows for the recovery and isolation of bm12-specific CD8 T cells that are intrinsically resistant to cyclosporine and rapamycin (i.e. resistant without any prior exposure to the agents) from C57BL/6 mice previously primed with a full-thickness bm12 skin graft. Recovery of such bm12-specific CD8 T cells that are intrinsically resistant to cyclosporine and rapamycin enabled the inventor hereof to newly identify the components of the heretofore unknown CsA/RAPA resistant TCR activation pathway. As described in detail herein, this also led to the identification of novel biomarkers for the CsA/RAPA-resistant CD8 T cell subset in mice and the subsequent confirmation of such biomarkers in humans with respect to the disease states of at least chronic allograft rejection and rheumatoid arthritis.

Conventionally, the only TCR activation pathway known for T cells is entirely dependent on a pathway interrupted (at different points) by calcineurin inhibitors (see TCR activation pathway 100 shown in subpart A of FIG. 1), or mTOR inhibitors that block signaling downstream of the IL-2 receptor (not shown). For reference, IL-2 is produced by the calcineurin-dependent pathway. There are in vitro CD4 and CD8 T cell CsA resistance phenomenon dependent on CD28 and IL-2; however, discordant with those in vitro findings, CD28 costimulatory blockade has been shown to be deleterious in MHC class II mismatched murine transplant models; and the inventor demonstrates that CD28 costimulation does not overcome inhibition of CD8bm12-1 proliferation by the combination of CsA and CH-223191 (FIG. 12b).

As previously noted, chronic allograft rejection is the major cause of organ failure and death in solid organ transplant patients. In cardiac transplantation, for example, conventional interventions that focus on atherosclerosis pathogenesis do not prevent cardiac allograft vasculopathy (CAV). Indeed, chronic allograft rejection progresses despite the administration of calcineurin inhibitors or mTOR inhibitors, other metabolic inhibitors of lymphocytes, or glucocorticoid therapy.

Animal models have clearly shown that chronic rejection vasculopathy is T-cell dependent and involves both CD4 and CD8 T cell subsets; however, in the presence of cyclosporine therapy it is the CD8 T cell subset that causes chronic rejection and its unique histopathology. The unusual histopathology (intimal proliferation and fibrosis instead of tissue necrosis) and resistance to calcineurin blockade evidences that CD8 T-cells driving chronic allograft rejection have an immunobiology very different from T-cells studied in standard mixed lymphocyte culture systems. Such differences significantly include a newly identified TCR activation/proliferation pathway 200 that is independent of calcineurin and NFAT (nuclear factor of activated T-cells), but Ahr-dependent (see subpart B of FIG. 1).

Elegant mouse CAV studies demonstrated an effector role for CD8 T cells in chronic rejection using MHC class II-mismatched bm12 cardiac allografts implanted into C57BL/6 mice. bm12 mice are isogenic with C57BL/6 mice except for a 3 amino acid change in the bm12 MHC II I-A$^b$ beta chain. The inventor's novel experimental system is based on a bm12 epithelial cell line as the "feeder" antigen presenting cell.

As previously noted, clinical experience and animal models have also shown that calcineurin inhibitors do not prevent CAV or BOS. The scientific literature supports a central role for allogeneic epithelial cells as primary targets for chronic allograft rejection, and CD8 T cells as effectors of chronic allograft rejection in when mice are treated with calcineurin inhibitor therapy. Experimentation in murine models has demonstrated that CD8 T cell-mediated chronic rejection includes recognition of MEW class II allo-antigens including I-A$^{bm12}$, and is dependent on production of IFN-γ but not killing pathways. Summation of the existing data implicates a noncytolytic IFN-γ-producing CD8 T cell subset with a TCR activation pathway resistant to calcineurin inhibitors as the mediator of chronic allograft rejection.

In light of the aforementioned data, the inventor hereof originally developed a methodology patent based on the novel T cell culture system based on bm12 origin epithelial cells, and their demonstrated ability to facilitate recovery of a cyclosporine-resistant bm12-specific CD8 T cell clone from a C57BL/6 mouse previously primed with a full-thickness bm12 skin graft as set forth in the related U.S. patent applications incorporated by reference herein. This CD8 T cell clone designated CD8bm12-1 met all the criteria identified by characterization of chronic allograft rejection in rodent models:
   a) Activation through the TCR complex (immobilized anti-CD3) induces proliferation that is intrinsically resistant to cyclosporine and rapamycin (see TCR activation pathway 200 of FIG. 1)
   b) Recognizes MHC class II alloantigen, specifically I-A$^{bm12}$
   c) Makes IFN-γ
   d) Is non-cytolytic
   e) In adoptive transfer into bm12 mice, causes histopathology consistent with chronic rejection In addition, CD8bm12-1 produces IL-17, a cytokine strongly linked to immunopathogenesis in rheumatoid arthritis and chronic allograft rejection.

Based on this bm12-specific CD8 T cell clone, a newly identified CsA/RAPA-resistant TCR activation pathway 200 (illustrated in subpart B of FIG. 1) was investigated and verified. As shown in FIG. 1, this novel alternative pathway 200 is independent of calcineurin/NFAT, incorporates some elements of B cell receptor signaling including Rasgrp 3 (ras guanyl-releasing protein 3 encoded by the RASGRP3 gene), Pla2g4a (phospholipase A 2g4a encoded by the PLA2G4A gene), and Prkcz (protein kinase C, zeta encoded by the PRKCZ gene), among others, and comprises a differential gene expression pattern as illustrated in FIG. 1, subpart B. Perhaps more specifically, the subset of CD8 T-cells that proliferate despite the presence of calcineurin or mTOR inhibitors utilize the secondary pathway 200 that goes from the TCR to Pla2g4a and activates Ahr (likely through the generation of an arachidonic acid metabolite). Ahr then pairs with RelB to trigger IL-2 independent T-cell proliferation; the AHR/RelB association has been shown by others. Furthermore, Scin is the structural gene under the control of Ahr and, as such, Scin expression reflects recent Ahr activation. Additionally (and importantly), the CD8 T cell subset that exhibits this Ahr-dependent pathway 200 lacks Lcp2, which is conventionally considered an indispensable TCR signaling molecule, thus identifying CD8bm12-1 as being representative of a novel previously unknown CD8 T cell subset.

These novel findings have numerous significant implications including, at least in part, those relative to the diagnosis and treatment of chronic allograft rejection and rheumatoid arthritis (both disease conditions in which this subset of CD8 T cells are effectors). Primarily, the Ahr-dependent TCR activation pathway 200 explains the conventional ineffectiveness of calcineurin and/or mTOR inhibitors with respect to the treatment and prevention of chronic allograft rejection. Indeed, treatment using a calcineurin and/or mTOR inhibitor alone only blocks the traditional calcineurin/NFAT dependent TCR activation pathway 100 and does nothing to prevent the cascade resulting from activation of the CD8 T cell subset exhibiting the Ahr-dependent pathway 200. Accordingly, in at least one exemplary embodiment of the present disclosure, a method of treating and/or preventing disease states where such subset of CD8 T cells is implicated (for example, chronic allograft rejection and rheumatoid arthritis) comprises inhibiting calcineurin and/or mTOR in combination with inhibiting Ahr (CH223191) to effectively block both TCR activation pathways 100, 200.

Additionally, because the T cell subset comprising Lcp2-negative CD8 T cells expands in subjects experiencing chronic allograft rejection and/or rheumatoid arthritis, an increase in mRNA for Pla2g4a (part of the resistance pathway 200 as shown in subpart B of FIG. 1) can be observed due to expansion of the CD8 T cell subset with the Ahr alternative pathway 200 in the presence of caclineurin inhibitors that block conventional T cell expansion during rejection. Uniquely, the Scin marker will be markedly elevated in CD8 T cells with recent AHR activation, indicative of ongoing active chronic rejection. Indeed, as described herein, Scin is one of the genes most highly upregulated when Ahr is activated and, as such, can be utilized as an indirect indicator of Ahr activation and an important surrogate marker for active chronic allograft rejection and/or rheumatoid arthritis.

Accordingly, in at least one exemplary method of the present disclosure, the method comprises identifying an upregulation of Scin in a subject to detect Ahr activation, which is indicative of the subject experiencing an inflammatory disease state mediated by the subset of CD8 T cells with the Ahr alternative pathway 200 (for example, active chronic allograft rejection and/or rheumatoid arthritis) as it indicates activation of the alternative, CsA/RAPA-resistant TCR activation pathway 200. Similarly, pursuant to the present disclosure, detection of increased Pla2g4a mRNA (as compared to healthy individuals or patients' pretransplant baseline) present in the circulated CD8 T cell pool is also indicative of the subject experiencing current, or having experienced a past, inflammatory disease state such as chronic allograft rejection and/or rheumatoid arthritis. Notably, the upregulation of Scin may be observed only in connection with active chronic allograft rejection and/or rheumatoid arthritis, whereas detection of increased amounts of Pla2g4a mRNA is indicative of the subject experiencing either current or past chronic rejection and/or rheumatoid arthritis.

Methods of treatment and novel therapeutic modalities are also provided based on the novel activation pathway identified herein and the resulting components thereof. For example, in at least one exemplary embodiment, a disease state that implicates the proliferation of the T cell subset comprising Lcp2-negative CD8 T cells may be treated by inhibiting Ahr and/or Pla2g4a in combination with a calcineurin inhibitor and/or a mTOR inhibitor. Such treatments may comprise the administration of a treatment (via administration of a compound or otherwise) comprising a therapeutically effective amount of an Ahr and/or a Pla2g4a inhibitor (such as, for example, CH-223191, which is a specific Ahr antagonist) and a therapeutically effective amount of a calcineurin and/or mTOR inhibitor (such as, for example, CsA, tacrolimus, and/or rapamycin). In at least one exemplary embodiment, the treatment may comprise CH-223191 and CsA.

The methods and investigations used to validate and confirm the findings from which the inventive methods and techniques of the present disclosure arise will now be described, followed by an analysis of the results of the same.

Methods

T Cell Clones

'Epithelial' C57BL/6 anti-H2-K$^{bm1}$ and anti-IA$^{bm12}$ CD8 T cell clones were derived using the inventor's novel experimental protocol and epithelial cell lines previously described in the Jayarapu Publication, which is incorporated by reference in its entirety herein. Female C57BL/6 mice (H-2$^b$) were separately primed with full thickness skin grafts from female bm1 (B6.C-H2bm1/ByJ) and bm12 (B6.C-H2bm12/KhEg) mice. 3×6 mm full thickness skin grafts were applied to the prepared tail dorsal surface, secured with 5-0 nylon sutures at 4 points and bandaged. The grafted skin healed in about 5 days and was rejected by day 14.

Mice were rested 8 weeks after graft rejection then primed splenocytes were collected. 5 million or 8 million primed splenocytes/well were added to 75% confluent monolayers of bm1 (Bm1.11) or bm12 (Bm12.4) epithelial cells in 24- or 6-well tissue culture plates containing RPMI complete medium (RPMI 1640, 10 mM Hepes, 10% characterized FBS, $5\times10^{-5}$M 2-mercaptoethanol, 25 uM gentamicin) supplemented with 500 pg/ml IL-1α, 500 pg/ml IL-6, 1 ng/ml IL-7, 4 ng/ml IL-15, 250 pg/ml TNF-α, 3 nM IFN4-α and 3 nM IFN-β. First passage on alloepithelial cells was the same cytokine milieu plus 10 units/ml recombinant human IL-2 (Chiron Corporation; Seattle, Wash.).

Polyclonal T cell populations were subsequently cloned by limiting dilution on mitomycin C-treated Bm1.11 or Bm12.4 alloepithelial cells to derive CD8bm1 and CD8bm12-1/CD8bm12-2 respectively. The CD8bm1 (H-2K$^{bm1}$ specific) and CD8bm12-1, CD8bm12-2 (H-2IA$^{bm12}$ specific) CD8 T cell clones were maintained on Bm1.11 and Bm12.4 alloepithelial cells respectively, pretreated with overnight with 3.6× polykine stock solution diluted to 1× (10 units/ml hIL-2, 500 pg/ml IL-la, 500 pg/ml IL-6, 1 ng/ml IL-7, 4 ng/ml IL-15, 250 pg/ml TNF-α, 100 unit/ml IFN4-α and 100 units/ml IFN-β) by addition of T cells the next day. The 750,000 T cells were added per 1.9 cm$^2$ epithelial monolayer (1.8 ml final volume); no irradiation, fixation, or mitomycin C treatment. T cells were passed every 4-6 days as per utilization/convenience. Murine recombinant cytokines were purchased from R&D Systems (Minneapolis, Minn.).

Cytokine Analysis

T cells were activated by immobilized anti-CD3 antibody (50 μl of 0.5 μg/ml 145-2C11 per well; NA/LE BD Pharmingen, San Jose, Calif.) without or with anti-CD28 antibody (50 μl of 1.0 μg/ml 37.51 per well; functional grade; Ebioscience, San Diego, Calif.). Generally, the immobilized anti-CD3 functions as a stimulus (T cell receptor complex) to activate the TCR pathway(s) 100, 200 in the cells, thus mimicking recognition of a specific antigen/WIC.

Immobilized antibody 96-well tissue culture plates (Costar) were prepared by incubating antibody in PBS overnight at 4° C. Wells were washed once with 150 μl of media prior to use. Supernatants were collected at 24 or 48 hours as indicated for specific experiments. Relative IL-2 (1A12 and 5H4; Thermo Scientific; Rockford, Ill.), IFN-γ (XMG1.2; Thermo Scientific), IL-10 (DESS-2A5 and SXC-1; BD Pharmingen), and IL-17a (TC11-18-H10.1 and TC11-8H4; Biolegend, San Diego, Calif.) levels were determined by ELISA according to the manufacturer's protocols. Recombinant murine IL-2, IL-10 (Thermo Scientific), IFN-γ (R&D Systems; Minneapolis, Minn.) and IL-17a (Biolegend) were used as standards.

Figure 5:
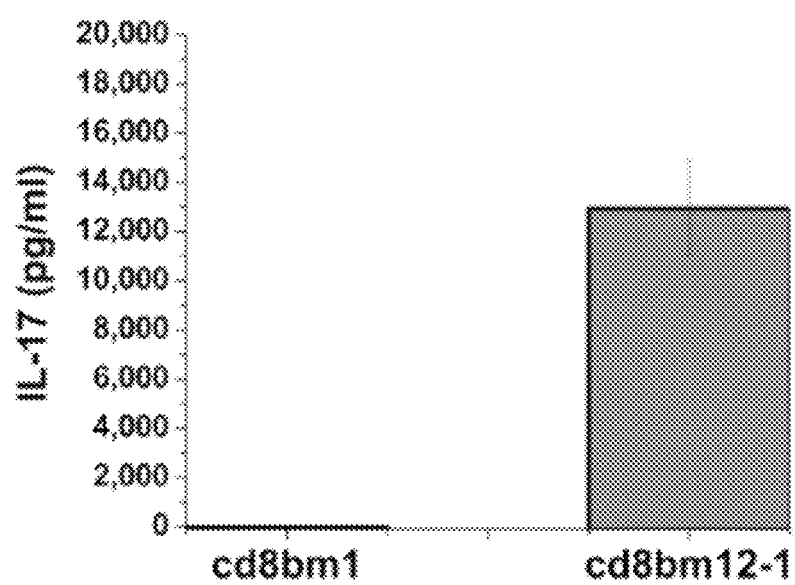
FIG. 5 shows a bar graph showing that CsA/RAPA-resistant CD8 T cell clone CD8bm12-1 makes IL-17 upon activation through the TCR by immobilized anti-CD3 antibody, while conventional CD8bm1 does not. IL-17 is a pathological cytokine in rheumatoid arthritis and chronic rejection.

FIG. 2A shows bar graphs of showing the levels of IFN-γ produced (in pg ml$^{-1}$) by the CD8 alloreactive T-cell clones activated by either Bm1.11 (white bars) or Bm12.4 (black bars). The results displayed in FIG. 2A demonstrate that activated CD8bm1, CD8bm12-1 and CD8bm12-2 produce IFN-γ and that CD8bm1 recognizes MHC class I H-2K$^{bm1}$, while CD8bm12-1 and CD8bm12-2 recognize MHC class II I-A$^{bm12}$. FIG. 2B shows that the MHC class II I-A$^{bm12}$ specific T cell clones CD8bm12-1 and CD8bm12-2 are non-cytolytic compared to CD8bm1 toward their respective allo-epithelial targets. Further, FIG. 5 shows a bar graph evidencing that CD8bm12-1 (i.e. the CsA/RAPA resistant CD8 T cell clone), but not CD8bm1, produced IL-17 when activated through the TCR by immobilized anti-CD3 antibody. Notably, IL-17 is a pathological cytokine in rheumatoid arthritis and chronic allograft rejection.

Cytolytic Assays

Lysis of allo-epithelial cell lines Bm1.11 and Bm12.4 was determined with an LDH release assay according to the manufacturer's protocol (CytoTox 96® NonRadioactive Cytotoxicity Assay; Promega).

Monoclonal Antibodies and Flow Cytometry

Murine T cells were stained with antibodies specific for murine CD4 (FITC-coupled YTS 191.1; Cedarlane Laboratories; Burlington, N.C.) and CD8a (PE-coupled 53-5.8; BD Biosciences). Human T cells were stained with antibodies specific for CD4 and CD8a (RPA-T4 FITC, RPA-T8 PE; Ebioscience) and analyzed on FacsCalibur Flow Cytometer.

Figure 4:
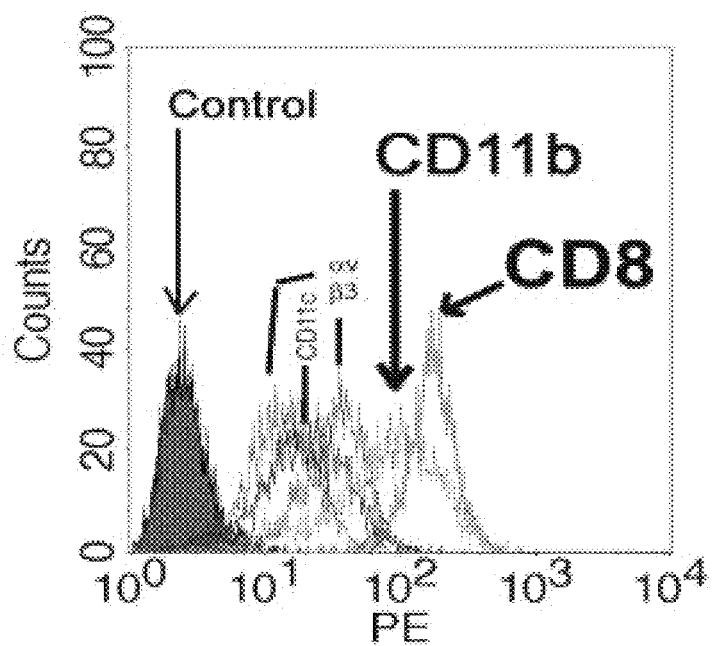
FIG. 4 shows flow cytometry data measuring cell surface phenotypes of T cell clone CD8bm1 and evidencing that CD8bm1 is a CD8 T cell clone.

FIG. 3 shows the flow cytometry data associated with cell surface phenotype measurements of CD8bm12-1, while FIG. 4 shows the flow cytometry data associated with cell surface phenotype measurements of CD8bm1; demonstrating that these are CD8 T cell clones.

Proliferation Assays

Proliferation assays were done with anti-CD3 (145-2Cl 1) without or with anti-CD28 (37.51). Antibodies in 50 μl of PBS/well were used to coat 96-well tissue culture plates (Costar) overnight at 4° C. Antibodies were shaken off and wells washed 1× with 150 μl of RPMI complete media prior to their use in proliferation assays. Experimental wells were pulsed with 0.5 μCi/well $^3$H-thymidine (ICN, Costa Mesa, Calif.) for 10-12 hours at 24-36 or 36-48 hours of the culture cycle. Cyclosporine A (Sigma Chemical Co.; St. Louis, Mo.) dissolved in 200 proof ethanol and CH-223191 (Calbiochem; San Diego, Calif.) dissolved in dimethylsulfoxide were used at indicated concentrations. The no treatment controls in each experiment included vehicle controls for both ethanol and dimethylsulfoxide.

Figure 6A:
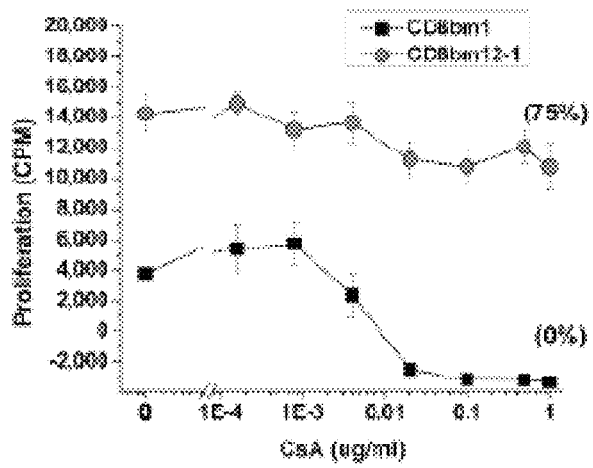
FIGS. 6A and 6B show plots of proliferation of CD8bm1 (■) and CD8bm12-1 (●) activated by immobilized anti-CD3 over a full range of cyclosporine A, with FIG. 6A=the results of experiment 1.
Figure 6B:
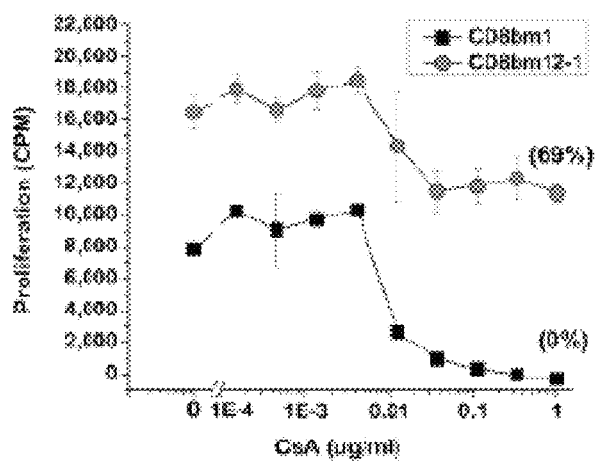

FIGS. 6A and 6B show proliferation plots of CD8bm1 (■) and CD8bm12-1 (●), both activated by immobilized anti-CD3 and exposed to a full range of cyclosporine A (the results shown in FIGS. 6A and 6B result from two separate experiments conducted). The graphs of FIGS. 6A and 6B support that CD8bm12-1 cells were resistant to cyclosporine A, while the proliferation of the conventional CD8bm1 clones was completely inhibited under the same conditions. Perhaps more specifically, CD8bm12-1 retained between about 69-75% of its proliferative capacity in the presence of 1 μg/m CsA when activated through the T cell receptor.

Figure 7:
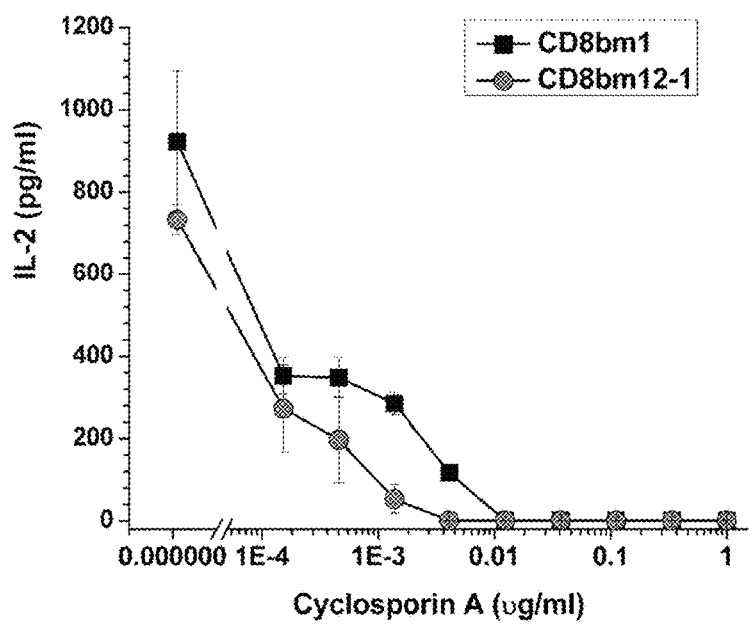
FIG. 7 shows a plot of IL-2 production by CD8bm1 (■) and CD8bm12-1 (●) activated by immobilized anti-CD3 over the full range of cyclosporine tested in the experiment associated with the results of FIG. 6B.
Figure 8:
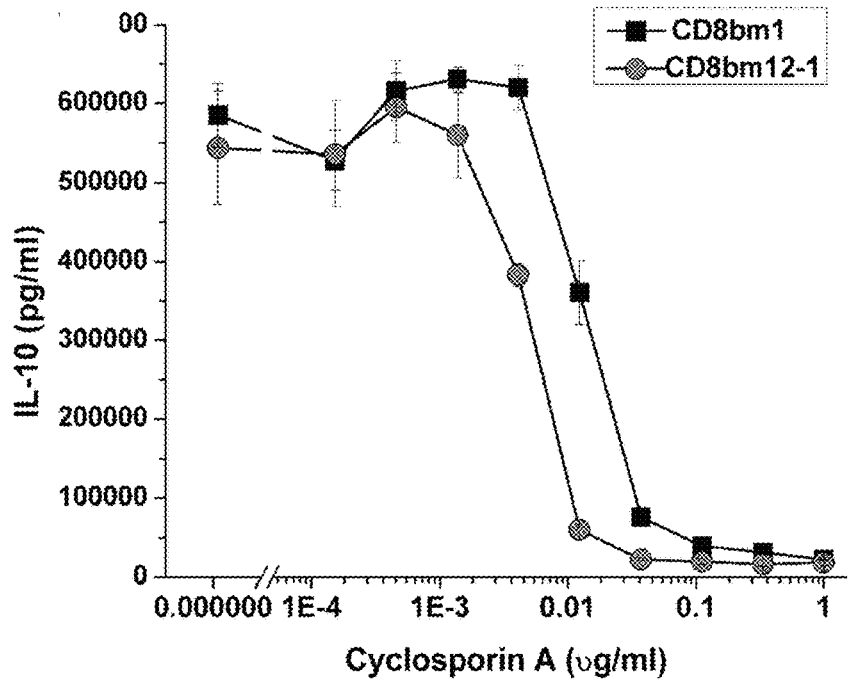
FIG. 8 shows a plot of IL-10 production by CD8bm1 (■) and CD8bm12-1 (●) activated by immobilized anti-CD3 over the full range of cyclosporine tested in the experiment associated with the results of FIG. 6B.
Figure 9:
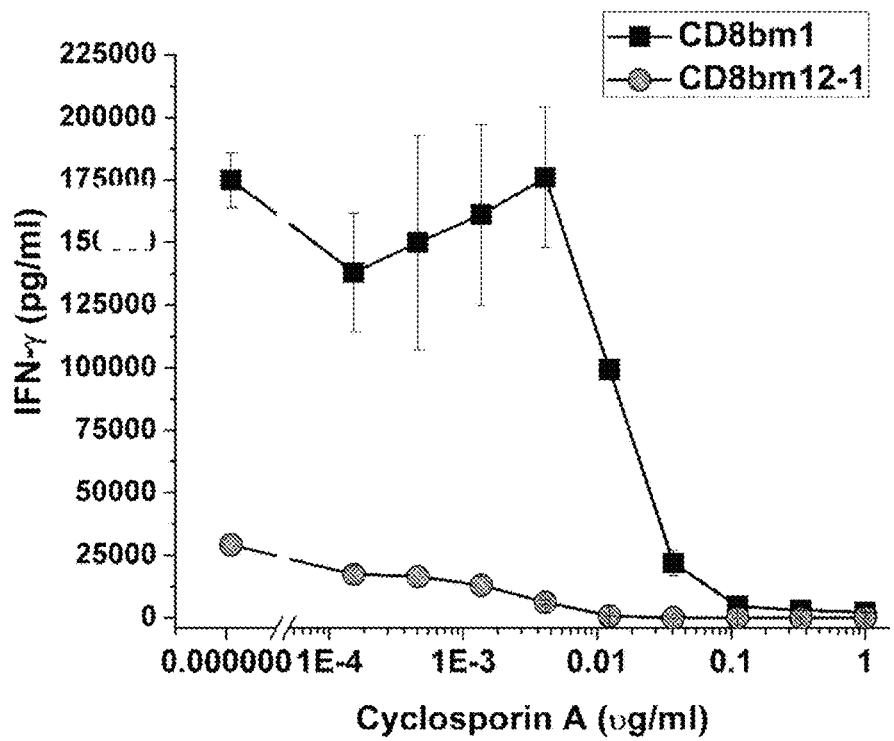
FIG. 9 shows a plot of Interferon-gamma production by CD8bm1 (■) and CD8bm12-1 (●) activated by immobilized anti-CD3 over the full range of cyclosporine tested in the experiment associated with the results of FIG. 6B.
Figure 10:
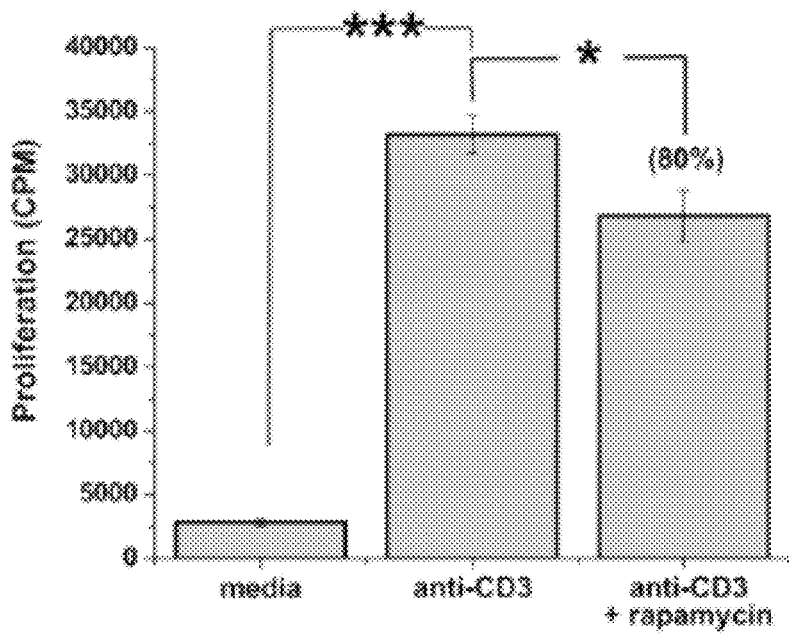
FIG. 10 shows a plot of proliferation of CsA/RAPA-resistant CD8bm12-1 cells exposed only to media (unactivated cells) and CD8bm12-1 cells activated by exposure to immobilized anti-CD3 antibody, and CD8bm12-1 cells activated by exposure to immobilized anti-CD3 antibody and in the presence of 25 nM rapamycin, with the CD8bm12-1 cells retaining 80% of its proliferative capacity when activated through the T cell receptor in the presence of 25 nM rapamycin. (***=p value<0.0005)

As part of the proliferation assays that examined the CsA-resistance of the CD8bm12-1 clones, IL-2, IL-10, and IL-γ production levels of the cells tested in FIG. 6B were also evaluated by ELISA according to the manufacturer's protocols. Specifically, FIG. 7 shows a plot of IL-2 production, FIG. 8 shows a plot of IL-10 production, and FIG. 9 shows a plot of IFN-γ production, all of CD8bm1 (■) and CD8bm12-1 (●) activated by immobilized anti-CD3 over a full range of cyclosporine A (0-1 μg/ml). As shown in FIGS. 7-9, IL-2 production by both CD8bm1 and CD8bm12-1 was completely inhibited by <0.3 μg/ml CsA, and both IL-10 and IFN-γ production in CD8bm1 and CD8bm12-1 are completely inhibited by <0.1 μg/ml CsA. These results, taken in concert with the data displayed in FIG. 6B, demonstrate CD8bm12-1 in the presence of 1 μg/ml CsA (FIG. 5) does not make calcineurin-dependent cytokines IL-2, IL-10, and IFN-γ. Proliferation of CD8bm12-1 in the presence of 1 ug/ml CsA occurs in a setting where IL-2 production is completely blocked, demonstrating that the CsA-resistant proliferation of CD8bm12-1 is IL-2 independent. Confirming that, CD8bm12-1 proliferation is also resistant to rapamycin that blocks signaling downstream of the IL-2 receptor (FIG. 10).

Furthermore, in reviewing the data of FIGS. 6B and 7 in particular, it is notable that the CD8bm12-1 clones retained their proliferative capacity at 1 μg/ml CsA despite the complete inhibition of IL-2 production at that concentration. In addition to the foregoing, this supports that CD8bm12-1 is intrinsically resistant to rapamycin, which acts downstream of the IL-2 receptor. Such rapamycin resistance was subsequently confirmed by performing a similar study with rapamycin. FIG. 10 shows a plot of the proliferation of CD8bm12-1 cells exposed to only media (unactivated cells) and CD8bm12-1 cells activated through the TCR by exposure to immobilized anti-CD3 antibody in the presence of 25 ηM rapamycin. Significantly, CD8bm12-1 retained about 80% of its proliferative capacity as compared to the activated CD8bm12-1 cells not exposed to rapamycin.

As described herein, a significant component of the novel TCR activation pathway 200 described herein is that it is Ahr-dependent, as opposed to being calcineurin-dependent as is the conventional TCR activation pathway 100 (see FIG. 1). To further confirm this Ahr-dependency and investigate the clinical implications thereof, the proliferative capacity CD8bm12-1 cells was investigated in the presence of an Ahr antagonist CH-223191.

Figure 11:
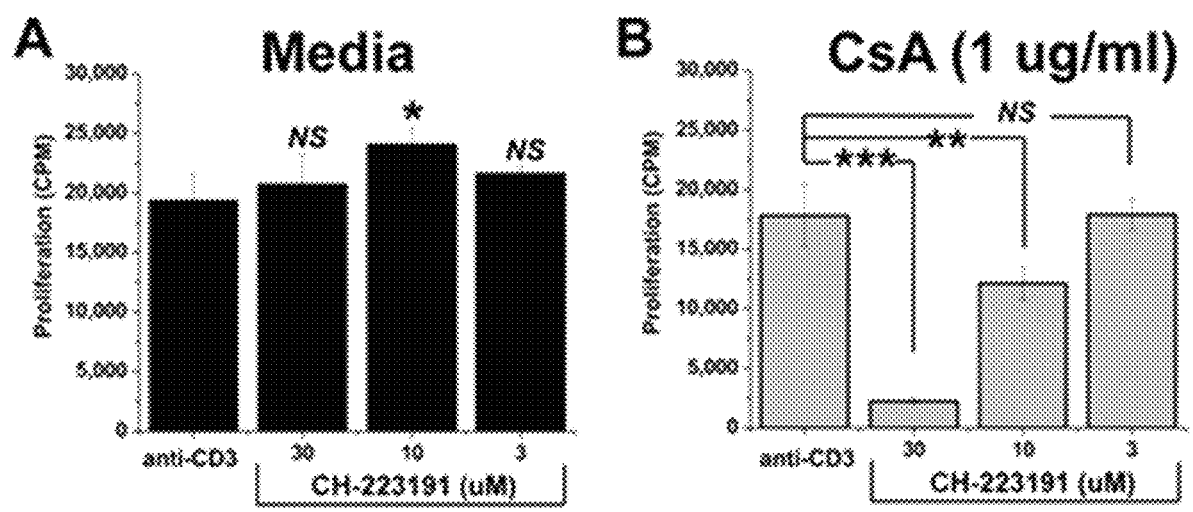
FIG. 11, subparts A and B, show bar graphs depicting data collected from CD8bm12-1 T-cells activated by immobilized anti-CD3 in the absence (subpart A) and presence (subpart B) of CsA and the absence and presence of varied concentrations of the Ahr inhibitor CH-223191 (μM). In media, activation of CsA/RAPA resistant CD8bm12-1 with anti-CD3 in the presence of an aryl hydrocarbon receptor inhibitor (CH-223191) had no effect on proliferation at 30 uM 10 uM or 3 uM. In media containing 1 ug/ml CsA, activation of CsA/RAPA resistant CD8bm12-1 with anti-CD3 in the presence of an aryl hydrocarbon receptor inhibitor (CH-223191) had a dramatic inhibitory effect on proliferation at 30 uM, moderate inhibitory effect at 10 uM, and no effect at 3 uM. Inhibition of calcineurin (CsA) and AHR (CH-223191) inhibits the CsA-resistant proliferation of CD8bm12-1; i.e. aryl hydrocarbon receptor activation is critical to the CD8bm12-1 cyclosporine resistant proliferation pathway.

As shown in FIG. 11, in media, activation of CsA/RAPA resistant CD8bm12-1 with anti-CD3 in the presence of varied concentrations of an Ahr inhibitor (CH-223191) alone had no discernable negative effect on the proliferation of the cells at 30 μM, 10 μM, or 3 μM (see subpart A). However, in 1 μg/ml CsA, activation of CsA/RAPA resistant CD8bm12-1 with anti-CD3 in combination with an Ahr inhibitor had a dramatic inhibitory effect on proliferative capacity at 30 moderate inhibitory effect at 10 and no effect at 3 μM (see subpart B of FIG. 11). As such, inhibition of calcineurin (CsA) and Ahr (CH-223191) inhibits the CsA resistant proliferation of CD8bm12-1, thus evidencing that Ahr activation is critical to the cyclosporine resistant activation/proliferation pathway. Additionally, treatment of the activated CD8bm12-1 CsA/RAPA-resistant cells with a combination of a calcineurin inhibitor and an Ahr inhibitor effectively inhibited proliferation of such cells.

Figure 12:
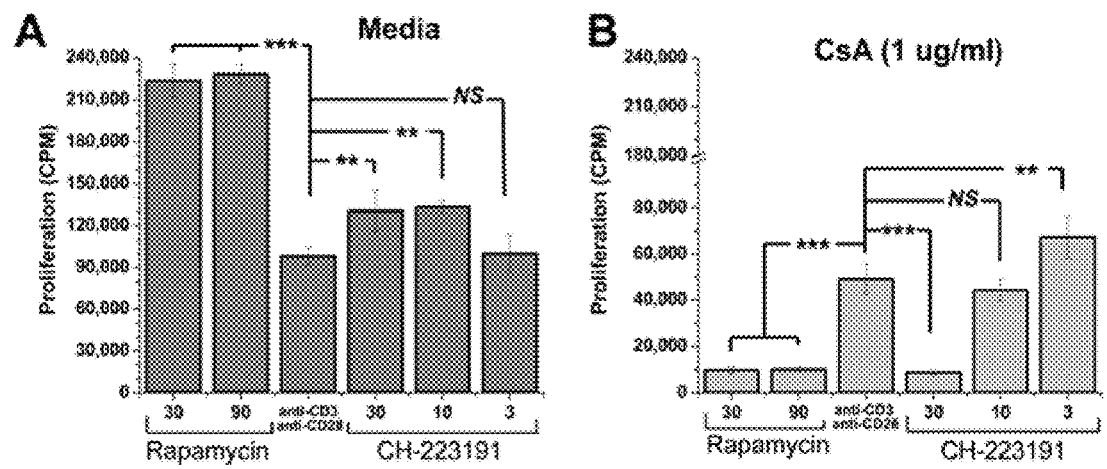
FIG. 12, subparts A and B, show bar graphs depicting data collected from CD8bm12-1 T-cells activated by immobilized anti-CD3/CD28 in the absence and presence of varied concentrations of the Ahr inhibitor CH-223191 (μM) and rapamycin (ηM). The specific data relates to: Subpart A) the proliferation in media without CsA; and Subpart B) the proliferation in the presence of 1 μg/ml CsA. In media, activation of CsA/RAPA resistant CD8bm12-1 with anti-CD3 and anti-CD28 in the presence of rapamycin enhanced proliferation while AHR inhibition had little effect. In media containing 1 ug/ml CsA, activation of CsA/RAPA resistant CD8bm12-I with anti-CD3 and anti-CD28 in the presence of 30 uM CH-223191 completely blocked proliferation. The combination of 1 ug/ml CsA and rapamycin also blocked proliferation; this combination very toxic and is not usable clinically.

FIG. 12 shows results of additional investigations of the CD8bm12-1 T cell clone utilizing an anti-CD3 and anti-CD28 in the presence of rapamycin, CsA, and/or an Ahr inhibitor.

Perhaps more specifically, FIG. 12 illustrates bar graphs depicting data collected from CD8bm12-1 T-cells activated by immobilized anti-CD3 and anti-CD28 in the absence and presence of varied concentrations of an Ahr inhibitor (μM) and rapamycin (TIM), both with (subpart B) and without (subpart A) 1 μg/ml CsA. In media, as shown in subpart A of FIG. 12, activation of CsA/RAPA-resistant CD8bm12-1 with both anti-CD3 and anti-CD28 in the presence of rapamycin enhanced proliferation, while Ahr inhibition (using CH-223191) had little discernable effect. However, as shown in subpart B of FIG. 12, activation of the CsA/RAPA-resistant CD8bm12-1 with anti-CD3 and anti-CD28 in the presence of either a combination of 1 μg/ml CsA and 30 μM CH-223191 or a combination 1 μg/ml CsA and rapamycin both blocked proliferation (i.e. was a potent inhibitor of CD8bm12-1 proliferation); i.e. that CD28 costimulation did not overcome AHR inhibitor blockade of CD8bm12-1 CsA-resistant proliferation. Notably, the combination of CsA and rapamycin is very toxic and not usable clinically; however, a pharmaceutical preparation containing a therapeutically effective dose of the combination of CsA and an Ahr inhibitor is a viable treatment option for clinical application in mammals that can effectively abrogate the CsA/RAPA-resistant TCR signaling pathway 200 in the presence of both the CD3 and CD28 costimulatory signal.

Adoptive Transfer of CD8bm12-1 into Bm12 Mice

Figures 13A, 13B, 13C:
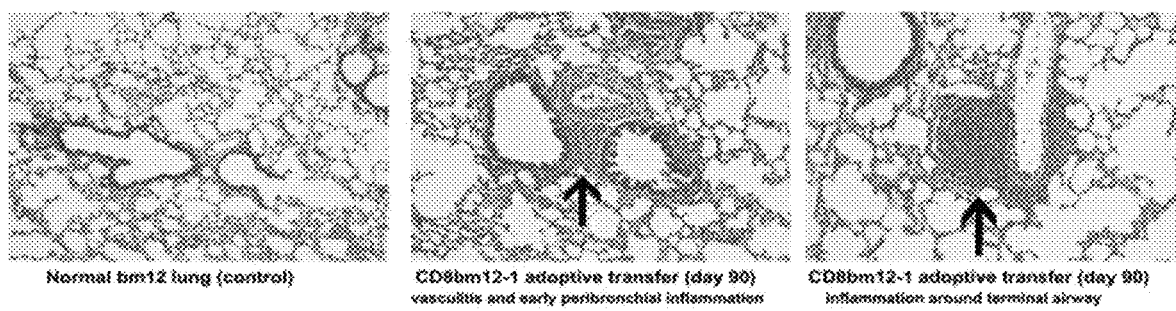
FIGS. 13A-13C show representative micrographs of stained lung sections from subject mice and support that adoptive transfer of CsA/RAPA resistant CD8bm12-1 into bm12 mice causes histopathology consistent with early bronchiolitis obliterans (chronic rejection histology) at 90 days.

To further verify that the CD8bm12-1 T-cell clones are, in fact, representative of the CsA/RAPA-resistant CD8 T-cells present in vivo that mediate chronic allograft rejection, rheumatoid arthritis, and/or any other disease state associated with activation of the novel TCR activation pathway 200 disclosed herein, CD8bm12-1 cells were transferred into bm12 mice via adoptive transfer techniques known in the art. Female bm12 mice received either 100 ul of PBS (25 ul via tail vein; 75 ul intradermal between shoulder blades) or 2 million CD8bm12-1 cells (500,000 via tail vein; 1.5 million intradermal between shoulder blades). 90 days later mice were killed and lungs processed for histopathology. As evidenced by the representative micrographs of stained lung sections from subject mice in FIG. 13, subparts A-C, the adoptive transfer of CsA/RAPA-resistant CD8bm12-1 into bm12 mice caused histopathology consistent with early BOS (lung chronic rejection) at 90 days, thus validating the CD8bm12-1 T cell clone causes immunopathology consistent with chronic rejection, and that this chronic rejection immunopathology would be CsA/RPA resistant based on the in vitro data presented, providing a link between such cells, the pathway 200, and chronic allograft rejection.

Gene Expression Microarray Analysis

CD8 T cell clones CD8bm1 and CD8bm12-1 were activated in 12-well tissue culture plates (Costar) coated at 4° C. overnight with 0.75 ml anti-CD3 antibody 145-2C110.5 μg/ml in PBS. Wells were washed 1× with RPMI media, then 3 million T cells added to each well in the absence and presence of 1 μg/ml cyclosporin A (Sigma Chemical Company; St. Louis, Mo.). Total RNA was isolated from each T cell clone 14 hours later using a protocol that included an RNAse-free DNAse I treatment step (RNeasy; Qiagen, Valencia, Calif.). The experiment was repeated four times to minimize background noise. Gene expression patterns were analyzed using the Affymetrix Mouse ST 1.0 Array that analyzes 28,853 murine genes. Genes up or down regulated 3-fold with p values<0.001 were considered in the final data analysis.

Figure 14:
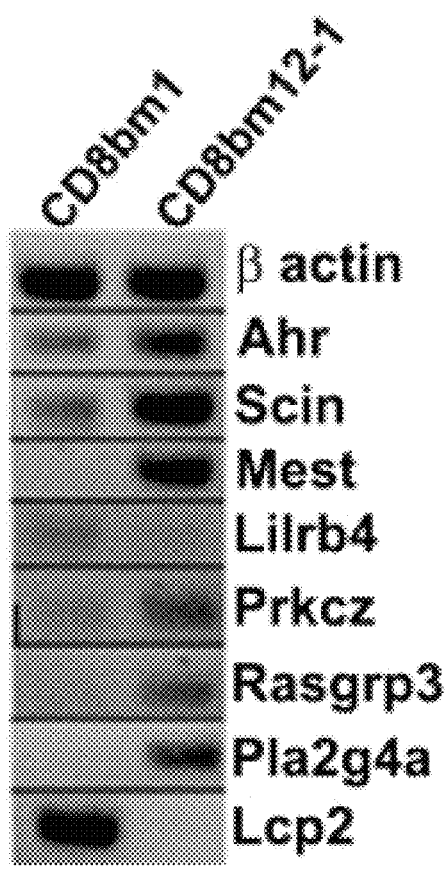
FIG. 14 shows an inverted image of an ethidium bromide stained gel showing the results of a gene expression microarray analysis comparing identified differences between conventional CD8bm1 and CsA/RAPA resistant CD8bm12-1 when activated by anti-CD3 in the presence of 1 µg/ml CsA using conventional RT-PCR. (Gene Expression Omnibus accession # GSE46122). Critical genes including Lcp2, Pla2g4a and Scin identified as being differentially expressed were confirmed by RT-PCR. Pla2g4a and Scin are important subset-specific biomarkers. Lcp2 is a critical component of conventional TCR signaling. Absence of Lcp2 expression in CsA/RAPA resistant CD8bm12-1 confirms that CD8bm12-1 represents a novel CD8 T cell subset with unique TCR activation signaling pathways.

FIG. 14 shows the resulting gene expression microarray analysis that compares identified differences between conventional CD8bm1 and CsA/RAPA-resistant CD8bm12-1 T cell clones (Gene Expression Omnibus accession #

GSE46122). Critical genes identified as being differentially expressed, including Lcp2, Pla2g4a, and Scin, were subsequently confirmed by RT-PCR (see below).

RT-PCR for Mouse Genes

Total RNA was isolated from CD8bm1 and CD8bm12-1 using RNeasy (Qiagen; Valencia, Calif.). Indicated quantities of total RNA were amplified with a one-step RT-PCR system (AccessQuick RT-PCR; Promega; Madison, Wis.) using primer pairs for the following biomarkers: beta actin, Ahr, Scin, Lilrb4, Lcp2, Mest, Rasgrp3, and Prkcz. Amplifications were done with a MJ Research PTC-200 Thermal Cycler using the following program: 1) 48° C. 45 min; 95° C. 1 min, then 2) 40 cycles 95° C. 20 sec; 57° C. 20 sec; 72° C. 40 sec, then 3) 72° C. 7 min. RT-PCR products were separated electrophoretically on 2% agarose gels containing ethidium bromide pursuant to methods known in the art; inverted images are shown for presentation purposes.

Human CD8 T Cell Purification and cDNA Preparation

A protocol for obtaining peripheral blood from human volunteers without and with a history of solid organ transplantation was submitted to and approved by the Indiana University Institutional Review Board. One healthy subject (control), two subjects that had undergone renal transplant (one experiencing active chronic rejection 2 years status post second renal transplant (early renal txp) and one with burned-out chronic rejection approaching dialysis (late renal txpl)), a subject that had undergone a liver transplant due to a Hepatitis C virus infection×5 years that was presenting with elevated levels of liver enzymes as compared to a normal, healthy individual (liver txpl HCV), and a subject with rheumatoid arthritis were recruited to participate in the study. The transplant subjects were on tacrolimus; the rheumatoid arthritis subject on leflunomide. Each subject donated 15 cc of blood drawn through a peripheral vein into EDTA blood tubes. Mononuclear fraction was purified by centrifugation as per the manufacturer's protocol (Lymphoprep; Axis-Shield, Oslo, Norway). 20-60 million purified peripheral blood mononuclear cells were cultured for each subject in RPMI complete media in tissue culture treated 100 mm petri dishes in a 5% $CO_2$ incubator for 1 h at 37° C. to partially remove adherent neutrophils and monocyte/macrophages, and to allow cells to disaggregate.

Non-adherent cells were recovered and then the "untouched" CD8 fraction was purified by magnetic bead separation according to the manufacturer's protocol (Miltenyi Biotech; Auburn, Calif.). Purified CD8 T cell fractions were stained for flow cytometry, and total RNA was isolated (RNeasy; Qiagen, Valencia, Calif.). 2 µg of total RNA per subject was converted to cDNA per manufacturer's protocol (iScript™ cDNA Synthesis Kit; Biorad, Hercules, Calif.) and stored at −80° C.

PCR amplification on indicated quantities of cDNA (RNA equivalents) in 25 µl total volume was done with a hot-start Taq polymerase according to manufacturer's protocol (Clontech) in an MJ Research PTC-200 Thermal Cycler using the following program: 1) 3 minutes at 95° C., 2) 95° C. 20 sec; 57° C. 20 sec; 72° C. 40 sec, then go to step 2 39 times, followed by 3) 72° C. 7 minutes for a total of 40 cycles. PCR products were separated electrophoretically on 2% agarose gels containing ethidium bromide pursuant to methods known in the art; inverted images are shown for presentation purposes.

RT-PCR for Human Biomarkers

Indicated quantities of cDNA were amplified with primers for beta actin, Scin, and Pla2g4a using iTaq™ DNA Polymerase according to the manufacturer's protocol (Biorad). Amplifications were done with a MJ Research PTC-200 Thermal Cycler using the following program: 1) Hot start 95° C. 3 min, then 2) 40 cycles 95° C. 20 sec; 57° C. 20 sec; 72° C. 40 sec, then 3) 72° C. 7 min. PCR products were separated electrophoretically on 2% agarose gels containing ethidium bromide; inverted images are presented.

Figure 15:
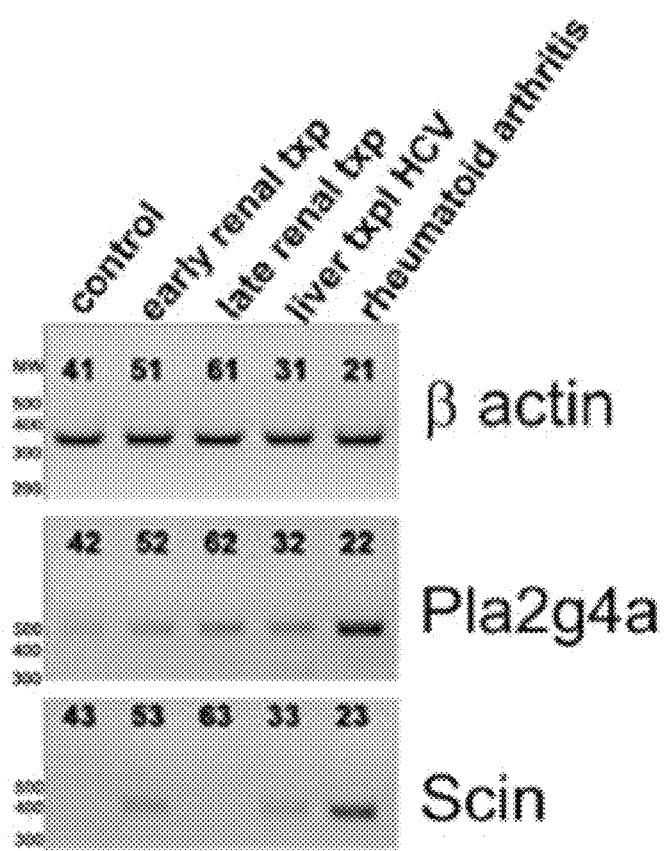
FIG. 15 shows an inverted image of an ethidium bromide stained gel showing differential levels of Pla2g4a and Scin in total RNA isolated from the circulating CD8 T cell pool of five human subjects by RT-PCR: 1) a healthy control subject (control), 2) an early renal transplant subject with active chronic rejection 2 years status post second renal transplant with worsening renal function (early renal txp), 3) a late renal transplant subject with burned out rejection approaching dialysis with no change in CrCl (late renal txpl), 4) a liver transplant subject for HCV×5 years with elevated liver enzymes (liver txpl HCV), and 5) a rheumatoid arthritis patient (CCP-positive). The transplant patients were on the calcineurin inhibitor tacrolimus; the rheumatoid arthritis patient on leflunomide. With a 40 cycle two step RT-PCR all transplant patients and the rheumatoid arthritis patient showed increased levels of Pla2g4a mRNA in the circulating CD8 T cell pool; only subjects with active disease (early txpl, liver transplant, and rheumatoid arthritis) had detectable levels of Scin mRNA in the circulating CD8 T cell pool based on 40 cycle RT-PCR with 150 ng total RNA equivalents. Beta actin amplification on 50 ng of total RNA equivalents served as an RNA quantity and quality control. Results evidencing that both Pla2g4a and Scin are practicable biomarkers for the CsA/RAPA-resistant CD8 T cell subset in humans.

FIG. 15 shows differential levels of Pla2g4a and Scin in total RNA isolated/purified from the circulating CD8 T-cell pool of the five subjects by RT-PCR. Beta actin amplification on 50 ng of total RNA equivalents served as an RNA quantity and quality control.

Results

As reported herein, the applicant's novel experimental system based on a bm12 epithelial cell line allowed for the recovery of IFN-γ producing CD8 T cell clones specific for I-A$^{bm12}$ with low cytolytic capability from C57BL/6 mice primed with a bm12 full thickness skin graft (designated CD8bm12-1). As supported by the data presented herein, the CD8bm12-1 clones utilized the alternative TCR activation pathway 200 and are thus representative of CD8 T-cell subsets that are effectors of chronic allograft rejection and rheumatoid arthritis. The novel experimental system included a parallel comparator T cell culture system based on a bm1 epithelial cell line that allowed for the recovery of a conventional cytolytic T lymphocyte clone (designated CD8bm1 and specific for K$^{bm1}$) from C57BL/6 mice primed with a bm1 full thickness skin graft, which was used in the investigative methods described herein for comparative purposes with CD8bm12-1.

CD8bm12-1, but not CD8bm1, was found to be intrinsically resistant to cyclosporine A and rapamycin. The ability of anti-CD3 activated CD8bm12-1 to proliferate in the presence of cyclosporine or rapamycin without prior exposure to either drug indicated that this CD8 T cell clone had a pre-existing TCR activation/proliferation pathway that was not dependent on calcineurin/NFAT and IL-2 respectively (i.e. the Ahr-dependent TCR pathway 200 (see subpart B of FIG. 1)).

Not only did CD8bm12-1 demonstrate a calcineurin/rapamycin resistant proliferation pathway, it mimicked the major features of the murine transplant literature associated with CD8 mediated chronic allograft rejection. Indeed, CD8bm12-1 was specific for MHC class II I-A$^{bm12}$, non-cytolytic, could be maintained ex vivo on bm12 epithelial cells, was polarized to make IFN-γ and IL-17, and caused early chronic rejection lung histopathology when adoptively transferred into bm12 mice.

The results of the investigations described herein and evidenced by the data reported in the present disclosure support the discovery chain including antigen specificity mimicking an extensive experimental literature utilizing bm12 to identify CD8 T cells as mediating chronic rejection (see FIG. 2A), assessment of cytolytic capability showing a noncytolytic CD8bm12-1 phenotype that explains the lack of acute necrosis during chronic rejection (see FIG. 2B) that was confirmed in vivo (see FIG. 13), CD8 T cell subset phenotype (see FIG. 3), cytokine polarization toward IFN-γ (see FIGS. 2 and 9) and IL-17 (see FIG. 5 showing that CD8bm12-1 makes IL-17 upon activation through the TCR by immobilized anti-CD3 antibody, while CD8bm1 does not), CD8bm12-1 cyclosporine-resistant proliferation (see FIGS. 6A/B) but not cytokine production including IL-2 (see FIGS. 7-9) and rapamycin-resistant proliferation (see FIG. 10) identifying the CD8bm12-1 pathway 200 as being calcineurin and IL-2 independent.

Additionally, the data supports the identification of the components of the CD8bm12-1 CsA/Rapa-resistant TCR activation/proliferation pathway 200 as described herein. An investigation of that pathway 200 was done by gene expression microarray analysis, with highlighted results listed below in Table 1. Perhaps more specifically, Table 1 lists the notable genes identified based on the microarray analysis that are unique to the CD3-activated CD8 T cells exhibit the Ahr-dependent TCR activation pathway 200. The data listed in Table 1 highlights the baseline differences (by way of expression fold increases) between CD3-activated CD8bm12-1 (C1) as compared to CD3-activated CD8bm1 T cells (C2).

TABLE 1

Baseline differences between CD3-activated CD8bm12-1 and CD3-activated CD8bm1 T cells
Fold increase of notable genes up & down regulated in activated CD8bm12-1 (C1)
versus activated Cd8bm1 not increased by CsA (C2).

| Gene | C1-fold‡ | C2-fold | Function |
|---|---|---|---|
| B cell signaling | | | |
| Prkcζ | 6.44 | 1.10 | PKCzeta-component of BCR signaling |
| PLCγ2 | 8.06 | −1.14 | Phospholipase C γ2-component of BCR signaling |
| Gpr183 | 7.64 | 1.46 | B cell migration |
| T cell signaling | | | |
| Lcp2 | −33.07 | −2.26 | SLP-76-critical for conventional TCR signaling |
| Dgkα | −10.77 | 1.14 | Diacyl glyceride kinase α-up regulated in anergic states |
| Lilrb4 | −12.09 | −2.27 | Leuk Ig-like receptor, group b, member4-coinhibitory receptor |
| Aryl hydrocarbon receptor (AHR) | | | |
| Scin | 196.46 | 1.19 | Scinderin-up regulated by activation of AHR |
| Pla2g4a | 43.9 | 1.38 | Phospholipase A2, group IV-signal transducer for AHR |
| Cell surface markers & cytokines | | | |
| CD7 | 16.5 | −1.12 | CD7 |
| Il18r1 | 29.8 | −2.71 | IL-18 receptor |
| IL-17a | 8.5 | −11.1 | IL-17a |
| IL-17f | 7.03 | −8.72 | IL-17f |
| Tgfb3 | 8.99 | 1.3 | TGF-beta 3 (fibrosis) |
| Other | | | |
| Sgk3 | 19.63 | −1.01 | downstream of PI-3 kinase (survival) |
| Gpr15 | 17.86 | 1.45 | G protein-coupled receptor 15 |
| Pls3 | 7.72 | 1.22 | unknown signaling molecule |
| Zfp187 | 9.17 | 1.03 | unknown transcription factor |

‡Welch T-test (log signal) pvalue $< 1 \times 10^{-7}$

Similarly, Table 2 shows those genes identified based on the gene expression microarray analysis upregulated in CD8bm12-1 cells versus CD8bm1 cells (C3) when both are activated in presence of 1 ug/ml CsA, along with fold induction in CD8bm12-1 cells by CsA (C2):

TABLE 2

Cyclosporin-specific changes induced-in and unique-to CD8bm12-1 T cells
CD8bin12-1/CsA vs. CD8bm1/CsA (C3)-genes unique to CsA treated CD8bm12-1 cells
CD8bin12-1/CsA vs. CD8bm12-1 (C2)-level of gene induction by CsA in Bm12-1 cells

| Gene | C3-fold* | C2-fold † | Function |
|---|---|---|---|
| Mest | 65.8 | 10.1 | ? fxn-upregulated in adipose tissue expansion |
| Padi2 | 29.8 | 6.48 | Peptidyl arginine deiminase 2-citrullination of proteins |
| Ahr | 34.95 | 2.88 | Aryl hydrocarbon receptor-multiple pathways including RelB |
| Klhl6 | 14.35 | 3.01 | Kelch-like 6-involved in B cell receptor(BCR) signaling |
| Rasgrp3 | 16.4 | 5.67 | BCR signaling downstream of PKCzeta |
| Klhl30 | 8.89 | 9.32 | unknown-protein-protein interaction domain |
| Trib2 | 7.78 | 4.42 | Tribbles homolog 2-growth advantage ex vivo |
| Rab17 | 5.5 | 5.46 | unknown-Ras family member |

*Welch T-test (log signal) pvalue $< 1 \times 10^{-9}$
† Welch T-test (log signal) pvalue $< 1 \times 10^{-7}$ The RT-PCR confirmation of the critical components of this data is shown in FIG. 14 including CD8bm12-1's unique expression of B cell receptor signaling components Rasgrp3, Pla2g4a, Prkcz, Klh16 among others, and the Ahr and a gene called Scin whose transcription is markedly upregulated when the Ahr is activated. Notably, both Pla2g4a and Scin are upregulated by activation of the CsA/RAPA-resistant TCR activation pathway 200 and, as such, in at least one exemplary embodiment of the present disclosure, can be used as important CD8 T-cell subset-specific biomarkers. Indeed, Scin in particular can be used as an accurate and easy-to-interpret biomarker as it is not detectable in a healthy subject. As such, any detection of Scin is indicative of a disease state mediated by CD8 T-cells that can proliferate via the CsA/RAPA-resistant TCR activation pathway 200.

In addition, CD8bm12-1 does not express a signaling molecule Lcp2 thought to be a universally critical component of conventional TCR signaling pathway 100. The absence of Lcp2 in a T cell clone that is fully activated by a CD3 stimulus and intrinsically resistant to cyclosporine and rapamycin identifies CD8bm12-1 as representative of a different kind of T cell representing an important new CD8 T cell subset. Similarly, the absence of Lcp2 expression in proliferating CD8 T cells is indicative of TCR activation pathway 200. Accordingly, in application, these differentially expressed genes/proteins can be leveraged with respect to the diagnosis and/or treatment of disease states where a subset of CD8 T-cells that utilize the CsA/RAPA-resistant TCR activation pathway 200 are effectors (such as, for example, chronic allograft rejection and rheumatoid arthritis).

The present disclosure confirms that the CsA/RAPA-resistant CD8bm12-1 TCR activation pathway 200-related activation of the Ahr is critical to the cyclosporine A resistant proliferation of CD8 T cells. The cyclosporine-resistant proliferation of CD8bm12-1 to an anti-CD3, or anti-CD3 plus anti-CD28, stimulus is completely blocked by addition of 30 uM of CH-223191, an Ahr antagonist (FIGS. 11 and 12, subpart B). In addition, the adoptive transfer of CD8bm12-1 into bm12 mice reproduces the histopathology of early chronic lung rejection (BOS) at 90 days (FIGS. 13A-13C), providing a tangible link between the TCR signaling pathway 200 identified in CD8bm12-1 and the immunohistopathology seen in chronic rejection.

Discovery of this previously unknown CD8 T cell subset and TCR activation/proliferation pathway 200 is relevant to diagnosing and treating human disease, specifically inflammatory conditions refractory to calcineurin and rapamycin therapy mediated by this novel CD8 T cell subset. Chronic allograft rejection and rheumatoid arthritis are two T cell-mediated conditions refractory to calcineurin inhibitor therapy.

The clinical investigation of specific subjects described above was performed to assess the role of the newly discovered CsA/Rapa-resistant CD8 T cell subset represented by CD8bm12-1. Five subjects reflecting health, active and burned out chronic rejection, and rheumatoid arthritis were recruited into an approved study. One healthy volunteer, two renal transplant patients (one with active chronic rejection and one with burned out chronic rejection), a liver transplant patient with elevated liver enzymes, and a rheumatoid arthritis patient. CD8 T cells were purified from the blood of each subject, total RNA isolated and converted to cDNA, then quantity of biomarker mRNA equivalents (cDNA) determined by PCR (i.e. two step RT-PCR).

As shown in FIG. 15, with a 40 cycle two step RT-PCR, all transplant subjects and the rheumatoid arthritis subject showed increased levels of Pla2g4a mRNA in the circulating CD8 T-cell pool, with only those subjects with active disease (early txpl, liver transplant, and rheumatoid arthritis) showing detectable levels of Scin mRNA in the circulating CD8 T-cell pool based on 40 cycle RT-PCR with 150 ng total RNA equivalents. Accordingly, in at least one exemplary embodiment of the present disclosure, the detection of elevated levels of Pla2g4a mRNA in the circulating CD8 T cell pool of a subject may be employed as a marker for expansion of the CsA/Rapa-resistant CD8 T cell subset, and detection of Scin (the gene whose transcription is regulated by the Ahr) as evidence for active chronic rejection or other disease state refractory to calcineurin and rapamycin therapy. The disease states for which the diagnostic and/or therapeutic methods provided herein are applicable may include inflammatory disease states (such rheumatoid arthritis or active chronic allograft rejection such as solid organ or bone marrow transplant, for example) or any other disease states that are mediated by the CD8 T cell subset that proliferate through the CsA/RAPA-resistant TCR activation pathway 200.

In at least one embodiment, a method of diagnosing the presence of a disease state in a subject may comprise the step of detecting the expression of a Scin biomarker in a circulating CD8 T cell population of the subject using RT-PCR, the techniques described below, or pursuant to techniques known in the art. As previously described in detail, because Scin expression is a direct byproduct of the TCR activation pathway 200 disclosed herein, Scin may be used as a simple yes/no biomarker in mammals (including, without limitation, humans) that is accurately indicative of the disease activity of an active disease state mediated by the CD8 T cell subset of note. Indeed, any expression of Scin in a subject's circulating CD8 T cell pool is indicative of an active disease state mediated by the CD8 T-cell subset utilizing the TCR activation pathway 200 because such pathway 200 is Ahr-dependent and Scin expression is directly regulated by Ahr.

Additionally or alternatively, a method of diagnosing the presence of a disease state in a subject mediated by CsA/RAPA-resistant CD8 T cells by detecting the expansion of a subset of activated CD8 T cells that are resistant to calcineurin and mTOR therapy and quantifying such expansion in the circulating CD8 T cell pool using the biomarker Pla2g4a. Perhaps more specifically, the step of detecting may comprise detecting an increased amount of Pla2g4a mRNA (as compared to an established standard—for example, the amount of Pla2g4a present in a healthy individual) present in a circulated CD8 T cell pool of the subject. In such methods, detection of an elevated amount of Pla2g4a is indicative of the subject experiencing a current, or having experienced a past, disease state.

In at least one embodiment of the aforementioned methods of diagnosis, the quantification of the Pla2g4a and Scin biomarkers may be accomplished by purifying CD8 T cells recovered from a mononuclear cell fraction of peripheral blood drawn from the subject (using, for example, magnetic bead purification as is known in the art and, in at least one exemplary embodiment a CD8+ T Cell Isolation Kit, human, #130-096-4950 commercially available from Miltenyi Biotech). Thereafter, the total RNA is isolated from the purified CD8 T cells (using, for example, RNeasy with a Dnase I step (or other e.g. DNA elimination columns) to eliminate genomic DNA (Qiagen) and one step RT-PCR (for example, using Promega AccessQuick™ RT-PCR System) of Pla2g4a and/or Scin mRNA are performed. A semi-quantitative visualization on ethidium bromide containing aragose gels may then be performed to display the results.

In other embodiments, CD8 purification can be accomplished by other means of cell sorting (for example, and without limitation, flow cytometry) and the biomarkers may be quantified at the mRNA level with real-time RT-PCR, or at the protein level with ELISA, or utilizing combined methodologies such as flow cytometry gated on CD8 T cells measuring intracellular Pla2g4a and/or Scin (frequency and/or levels).

Therapeutic treatment methods and strategies are also provided based on the findings of present disclosure and, in at least one embodiment, are based on the concept of concurrent disruption of both the Ahr-dependent TCR activation pathway 200 and the conventional TCR activation pathway 100. Furthermore, the in at least one embodiment, an exemplary method for treating a disease state that is mediated by a CD8 T cell subset that proliferates through the CsA/RAPA-resistant TCR activation pathway 200 is provided and comprises the step of administering a pharmaceutical preparation to a subject, the pharmaceutical preparation comprising a therapeutically effective dose of both a calcineurin and/or mTOR inhibitor(s) and an Ahr antagonist to effectively block both TCR activation pathways 100, 200 and stop and/or prevent the progression of the disease state. In at least one embodiment, such a pharmaceutical preparation may comprise a combination of therapeutically effective doses of cyclosporine A and CH-223191. Alternatively, such a pharmaceutical preparation may comprise a combination of therapeutically effective doses of rapamycin and/or tacrolimus, and CH-223191. Still further, in at least one embodiment, the Ahr antagonist may be substituted for a Pla2g4a inhibitor or, if desired, the Pla2g4a inhibitor may be used included in a formulation with a calcineurin and/or mTOR inhibitor(s) and an Ahr antagonist.

While various embodiments of compositions and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A method for treating a mammal suspected of having chronic allograft rejection or rheumatoid arthritis comprising the steps of:
    obtaining or having obtained an amount of peripheral blood from a mammal;
    purifying a population of CD8 T cells collected from the peripheral blood;
    isolating RNA from the purified CD8 T cells;
    quantifying a level of expression of a Scin biomarker in the isolated RNA;
    diagnosing the mammal with active chronic allograft rejection or rheumatoid arthritis if the Scin biomarker is expressed in the isolated RNA; and
    administering or having administered to the diagnosed mammal a therapeutically effective dose of a drug therapy for treatment of chronic allograft rejection or rheumatoid arthritis.

2. The method of claim 1, wherein the population of CD8 T cells is a circulating CD8 T cell population from a mononuclear cell fraction of the peripheral blood.

3. The method of claim 1, wherein:
    the step of purifying a population of CD8 T cells is performed using magnetic bead purification; and
    the step of quantifying a level of expression of a Scin biomarker further comprises performing reverse transcription polymerase chain reaction on the isolated RNA and producing a semi-quantitative visualization of the level of expression of the Scin biomarker on ethidium bromide-containing agarose gels.

4. The method of claim 1, wherein the mammal is a human and the Scin biomarker is a human biomarker.

5. The method of claim 1, wherein the level of expression of the Scin biomarker is indicative of the subset of CD8 T cells proliferating through an Ahr-dependent T-cell receptor signaling pathway.

6. The method of claim 1, wherein the step of purifying a population of CD8 T cells is performed using a cell sorting technique.

7. The method of claim 1, wherein the step of quantifying a level of expression of a Scin biomarker further comprises quantifying the level of expression of the Scin biomarker at a mRNA level using quantitative real-time RT-PCR or at a protein level using enzyme-linked immunosorbent assay.

8. The method of claim 1, wherein the step of quantifying a level of expression of a Scin biomarker further comprises utilizing flow cytometry gated on CD8 T cells to measure intracellular frequency and/or levels of the Scin biomarker.

9. The method of claim 1, wherein the drug therapy comprises:
    a therapeutically effective dose of a combination of (a) an Ahr antagonist and (b) one or both of a a calcineurin inhibitor and a mTOR inhibitor; or
    a therapeutically effective dose of a combination of a tacrolimus and an Ahr antagonist.

\* \* \* \* \*